(12) United States Patent
Marion

(10) Patent No.: US 11,530,241 B2
(45) Date of Patent: Dec. 20, 2022

(54) PEPTIDES FOR TREATMENT AND PREVENTION OF NONALCOHOLIC FATTY LIVER DISEASE AND FIBROSIS

(71) Applicants: UNIVERSITE DE STRASBOURG, Strasbourg (FR); INSERM (INSTITUT NATIONAL DE LA SANTÉ ET DE LA RECHERCHE MÉDICALE), Paris (FR)

(72) Inventor: Vincent Marion, Lipsheim (FR)

(73) Assignees: UNIVERSITE DE STRASBOURG, Strasbourg (FR); INSERM (INSTITUT NATIONAL DE LA SANTÉ ET DE LA RECHERCHE MÉDICALE, Paris (FR)

( * ) Notice: Subject to any disclaimer, the term of this patent is extended or adjusted under 35 U.S.C. 154(b) by 285 days.

(21) Appl. No.: 16/772,178

(22) PCT Filed: Dec. 14, 2018

(86) PCT No.: PCT/EP2018/085071
§ 371 (c)(1),
(2) Date: Jun. 12, 2020

(87) PCT Pub. No.: WO2019/115812
PCT Pub. Date: Jun. 20, 2019

(65) Prior Publication Data
US 2021/0087230 A1    Mar. 25, 2021

(30) Foreign Application Priority Data

Dec. 14, 2017 (EP) .................................... 17306772
Jun. 22, 2018 (EP) .................................... 18305797

(51) Int. Cl.
| | |
|---|---|
| *A61K 38/16* | (2006.01) |
| *C07K 14/00* | (2006.01) |
| *C07K 7/08* | (2006.01) |
| *A61P 1/16* | (2006.01) |
| *A61K 38/45* | (2006.01) |
| *C12N 9/12* | (2006.01) |
| *A61K 38/00* | (2006.01) |

(52) U.S. Cl.
CPC ................ *C07K 7/08* (2013.01); *A61K 38/16* (2013.01); *A61K 38/45* (2013.01); *A61P 1/16* (2018.01); *C07K 14/00* (2013.01); *C12N 9/12* (2013.01); *C12Y 207/11013* (2013.01); *A61K 38/00* (2013.01)

(58) Field of Classification Search
CPC ................................ A61K 38/16; C07K 14/00
See application file for complete search history.

(56) References Cited

U.S. PATENT DOCUMENTS

| | | | |
|---|---|---|---|
| 10,821,159 | B2 | 11/2020 | Marion et al. |
| 2020/0216504 | A1 | 7/2020 | Marion et al. |
| 2020/0368314 | A1 | 11/2020 | Marion et al. |
| 2021/0069301 | A1 | 3/2021 | Marion et al. |

FOREIGN PATENT DOCUMENTS

| | | |
|---|---|---|
| CN | 102 477 074 | 9/2013 |
| EP | 0 251 244 | 1/1988 |
| WO | WO 00/18895 | 4/2000 |
| WO | WO 2015/114062 | 8/2015 |
| WO | WO 2017/036852 | 3/2017 |
| WO | WO 2019/002583 | 1/2019 |
| WO | WO 2019/025620 | 2/2019 |

OTHER PUBLICATIONS

Moya, M. et al. "Foxa 1 Reduces Lipid Accumulation in Human Hepatocytes and Is Down-Regulated in Nonalcoholic Fatty Liver" *PLoS ONE*, Jan. 16, 2012, pp. 1-17, vol. 7, No. 1, e30014.
Samuel, V. T. et al. "Inhibition of protein kinase Cε prevents hepatic insulin resistance in nonalcoholic fatty liver disease" *The Journal of Clinical Investigation*, Mar. 2007, pp. 739-745, vol. 117, No. 3.
Written Opinion in International Application No. PCT/EP2018/085071, dated Apr. 8, 2019, pp. 1-8.

*Primary Examiner* — Lianko G Garyu
(74) *Attorney, Agent, or Firm* — Saliwanchik, Lloyd & Eisenschenk

(57) ABSTRACT

The present invention relates to peptides for the treatment or prevention of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma or fibrosis, especially liver fibrosis.

8 Claims, 13 Drawing Sheets
Specification includes a Sequence Listing.

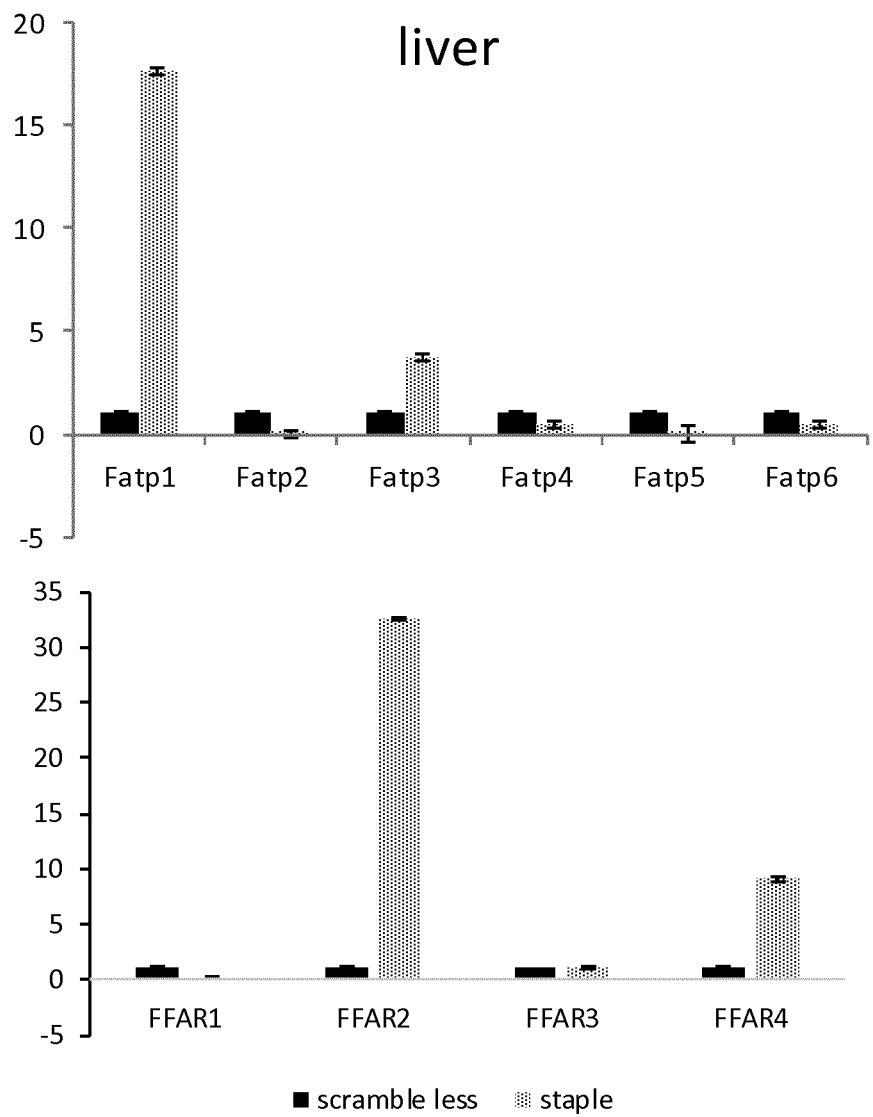

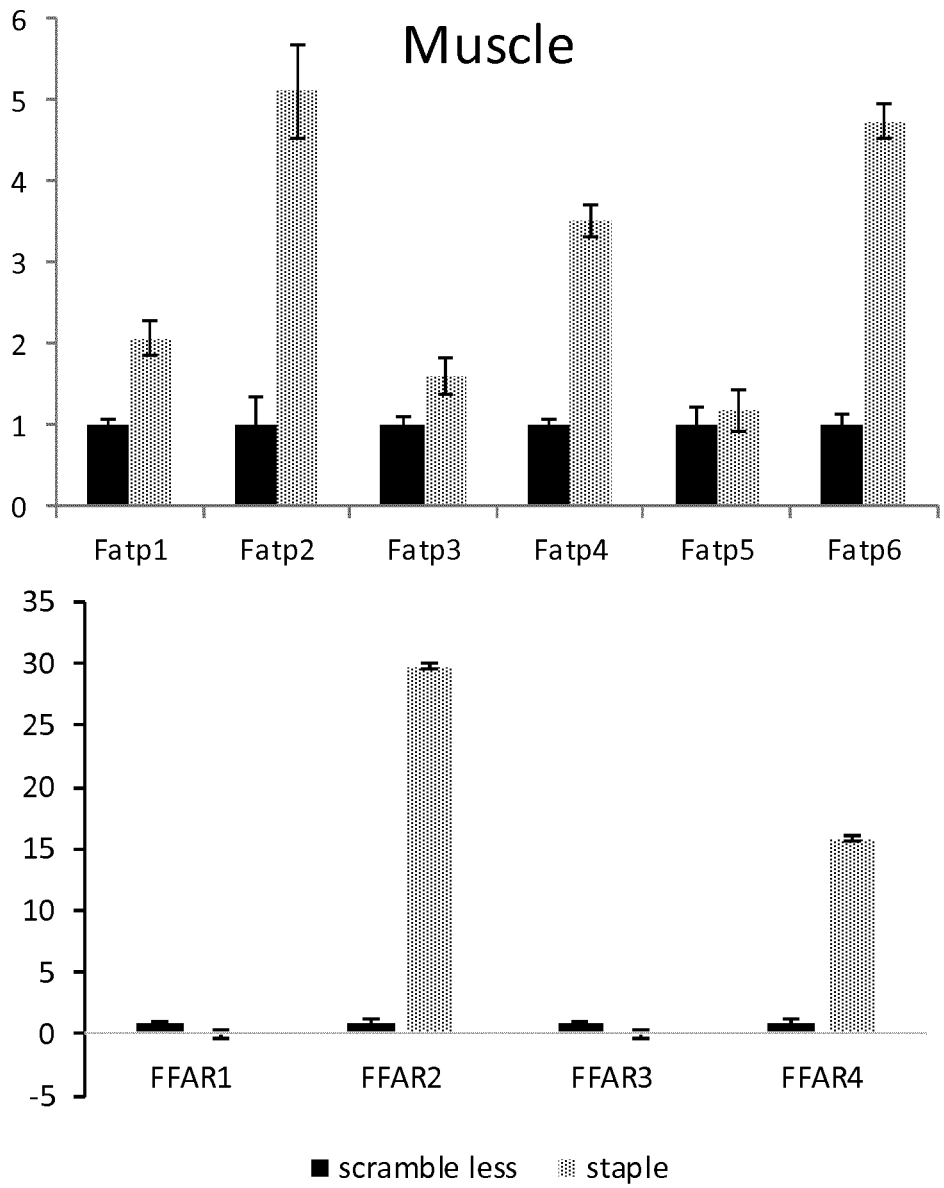

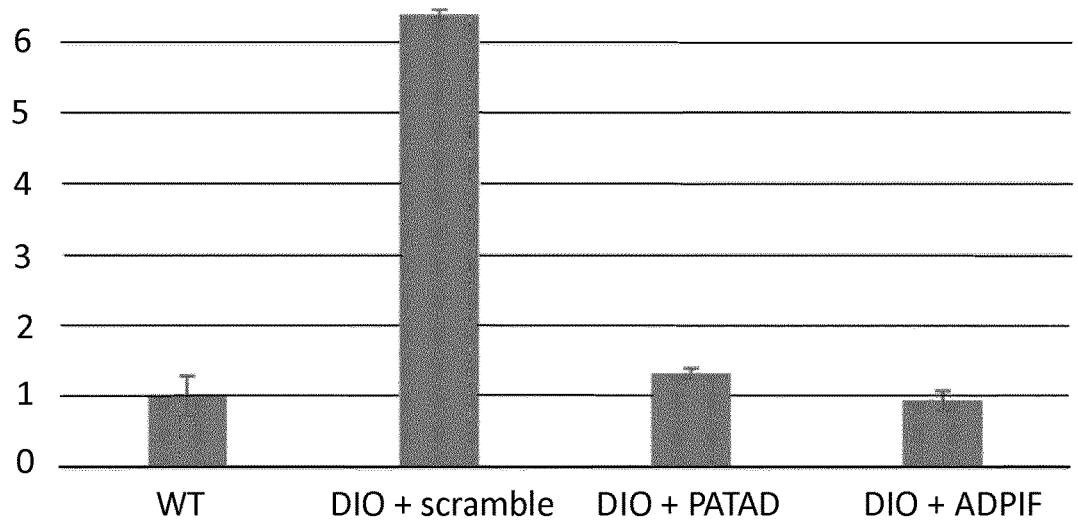
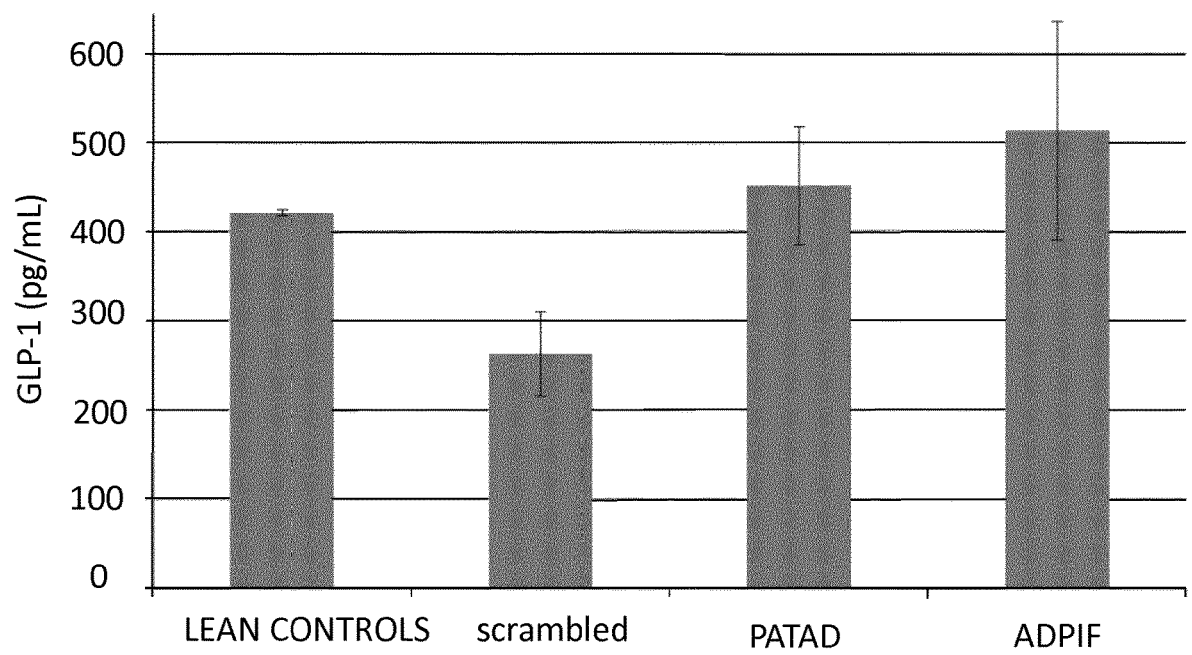

AdipoRed staining ratio liver/mice/days of age

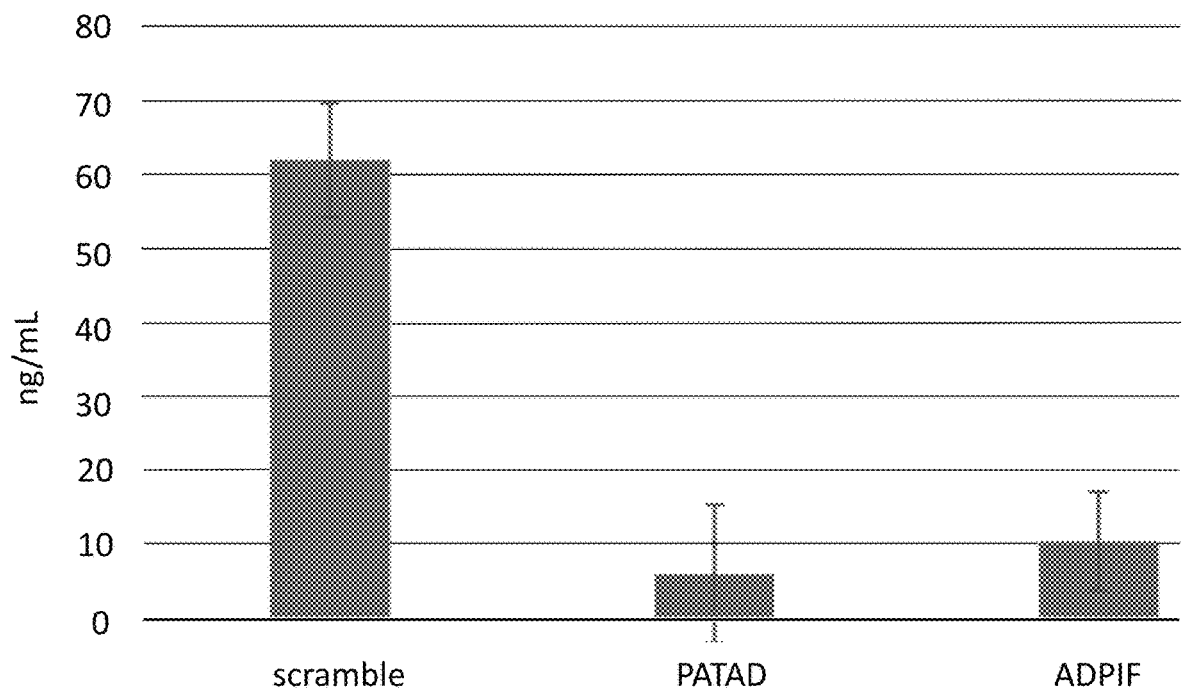
FIGURE 3C - AST
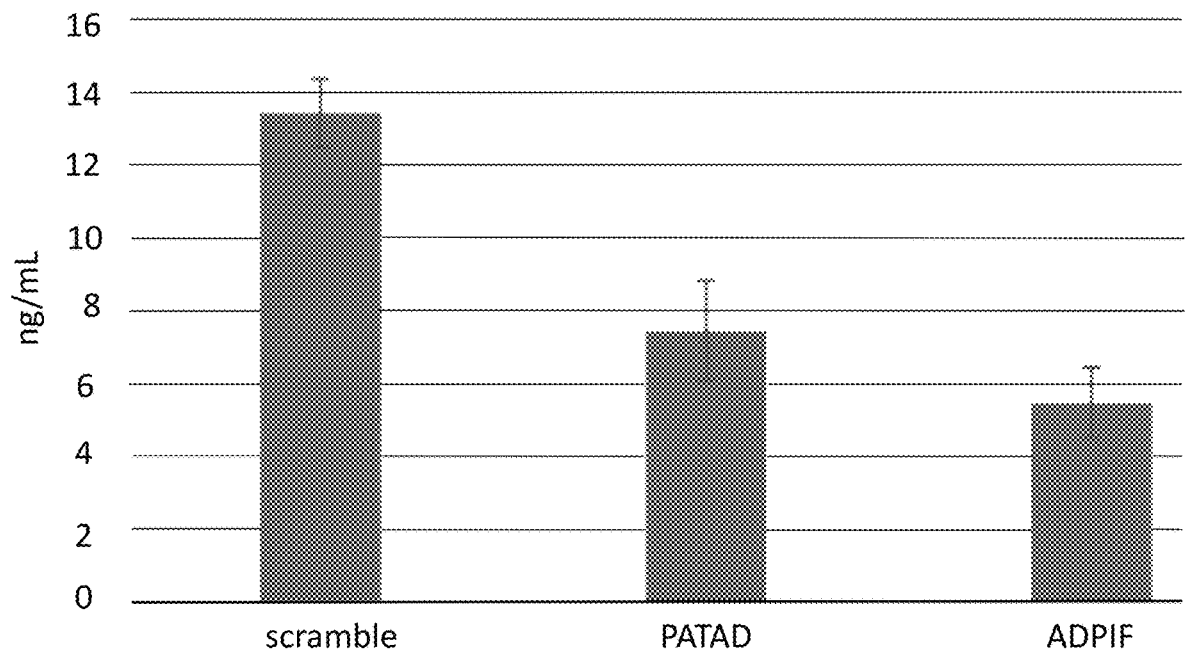
FIGURE 3D - ALT

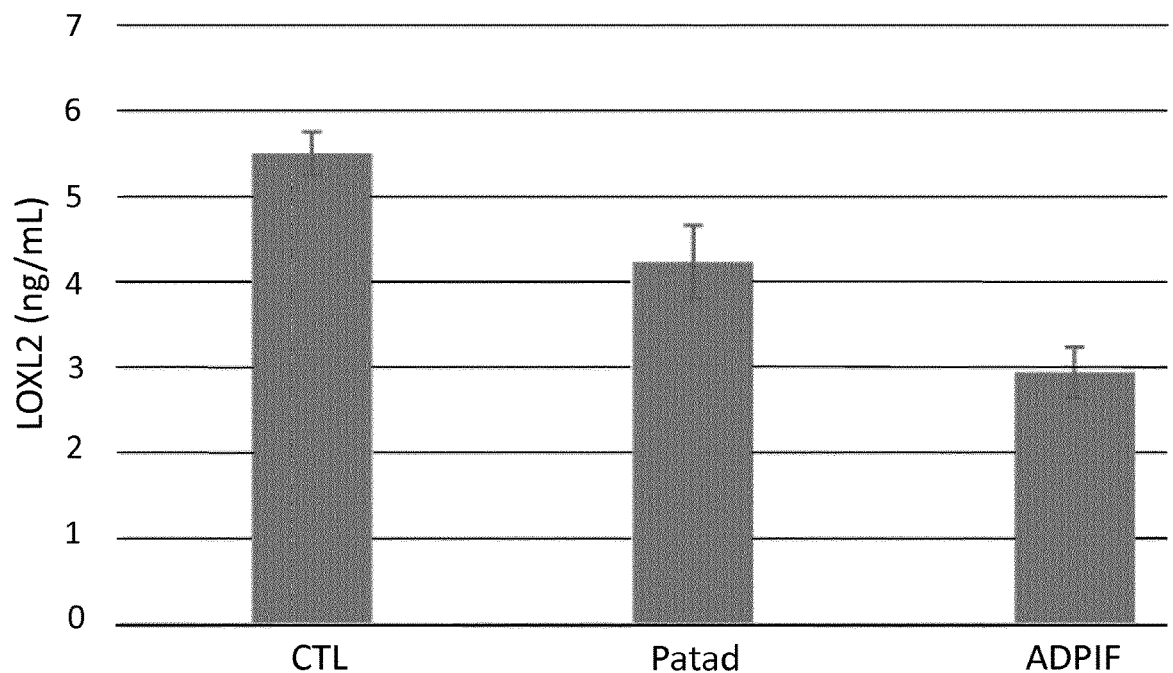
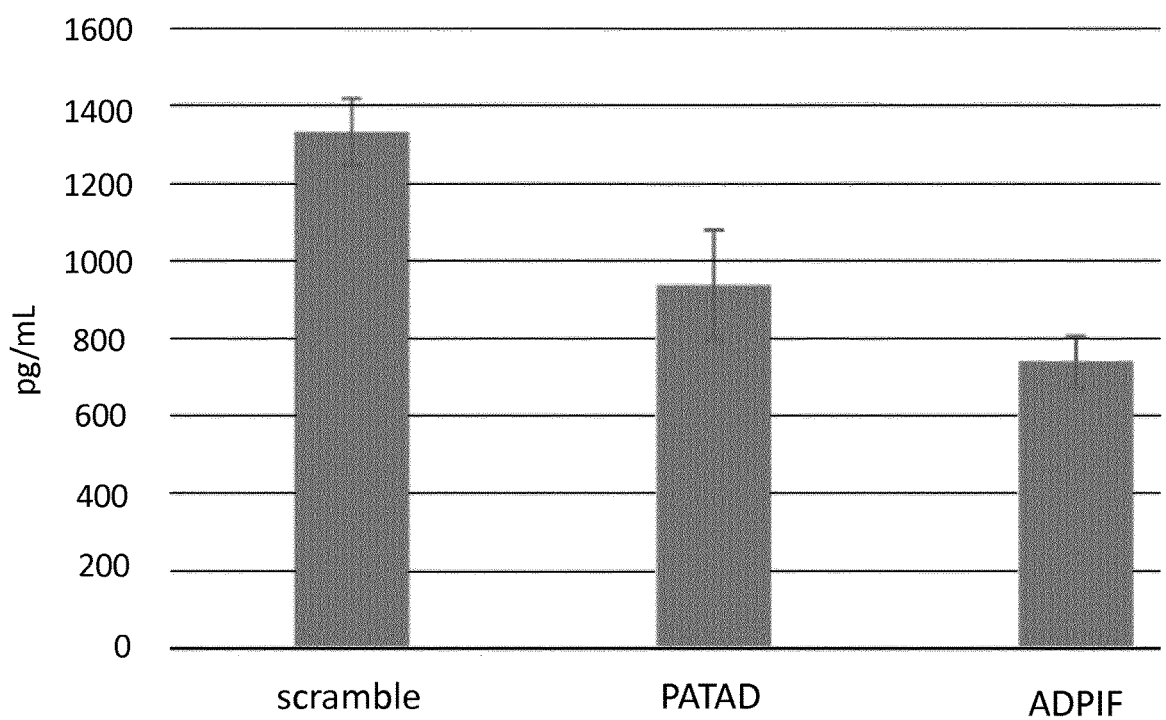

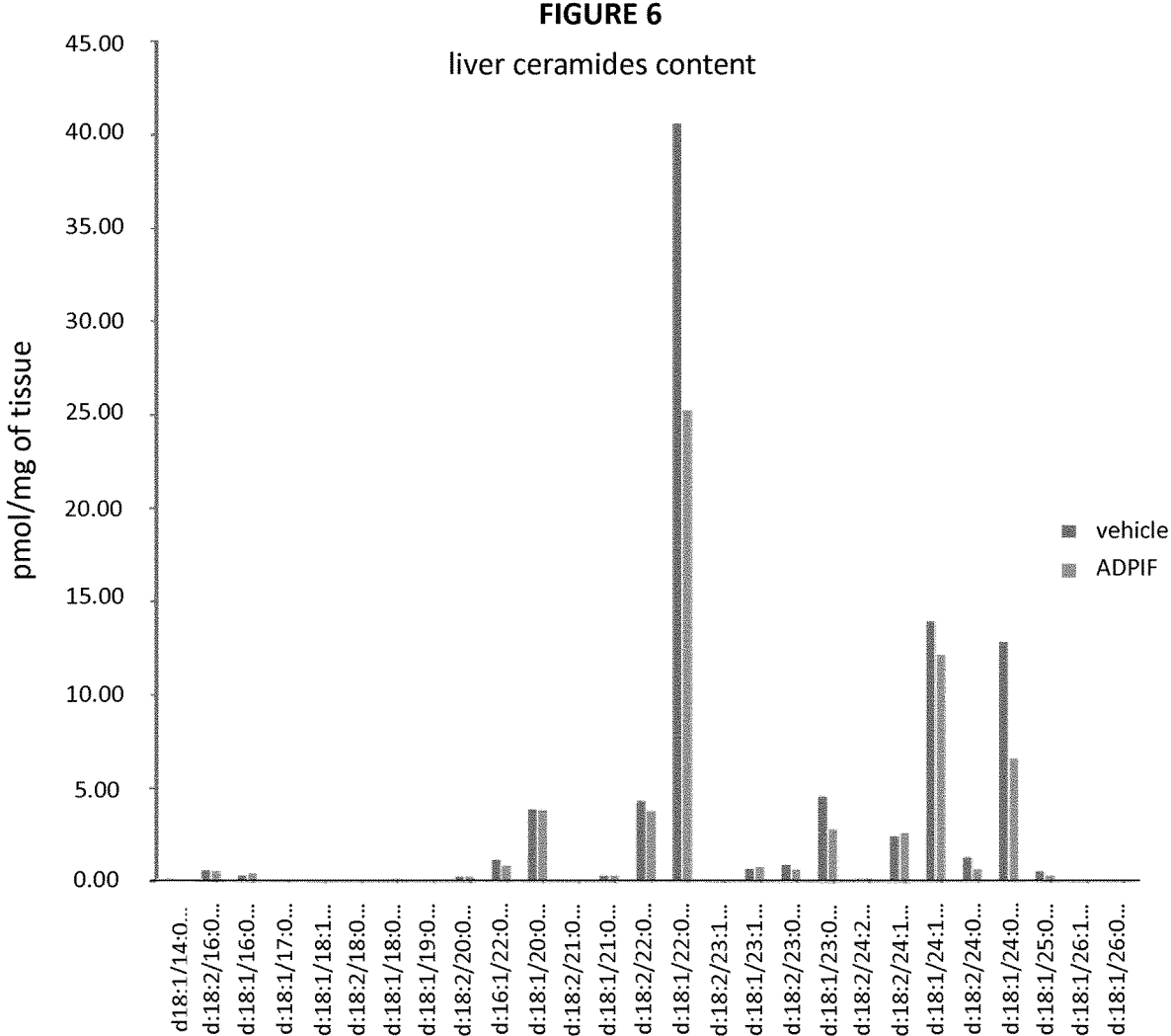
FIGURE 6
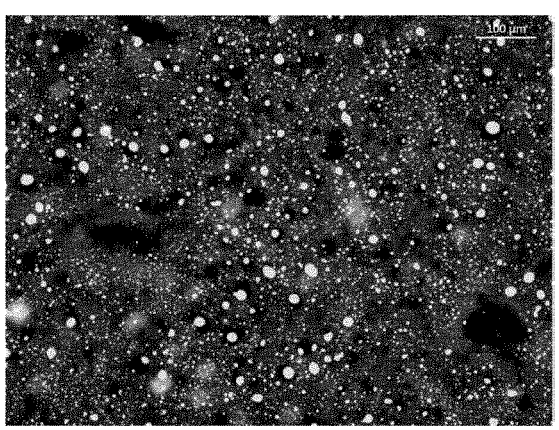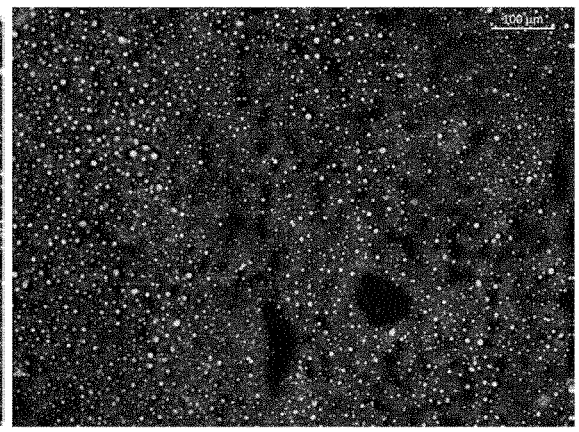
FIGURE 7

Fasn : Fatty acid synthase
Acc : Acetyl-CoA carboxylase
Srebf1 : Sterol regulatory element-binding transcription factor 1

FIGURE 10A – Pancreas
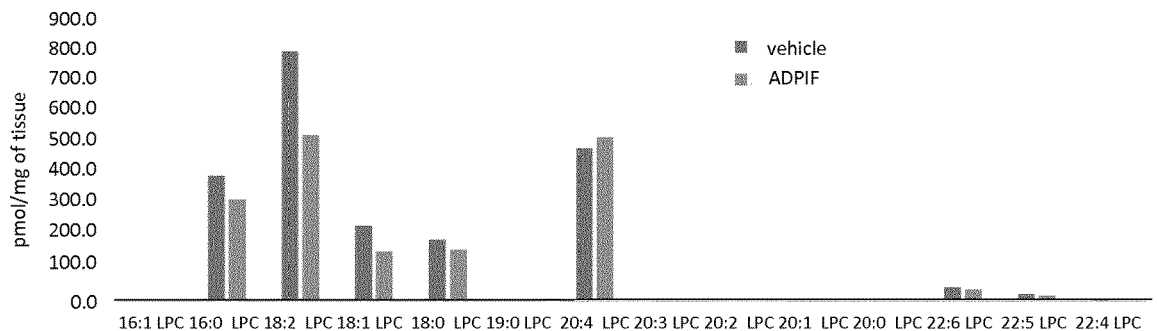
FIGURE 10B – Adipose tissue
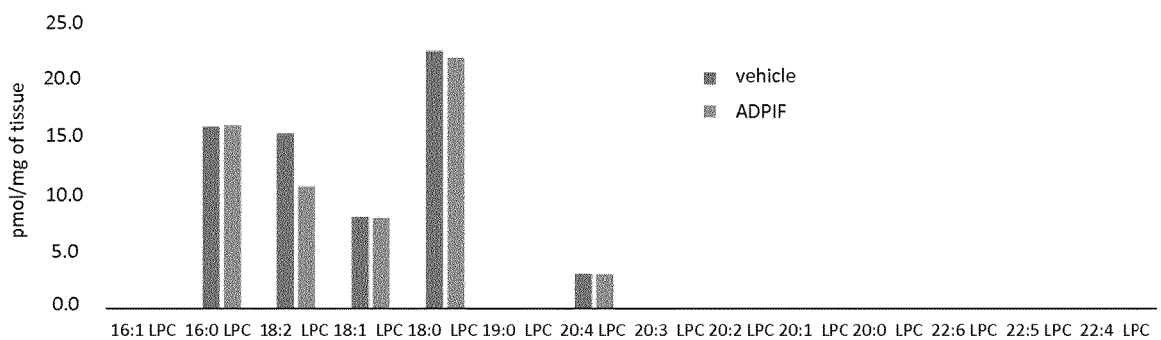
FIGURE 10C - Liver
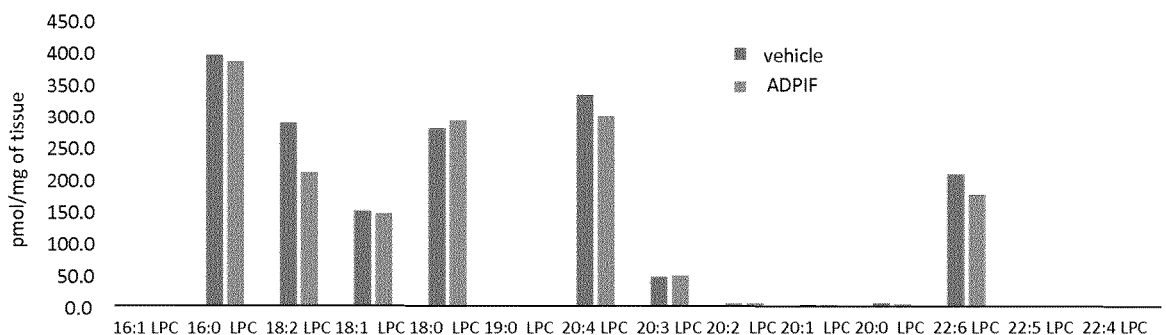
FIGURE 10D – Plasma levels
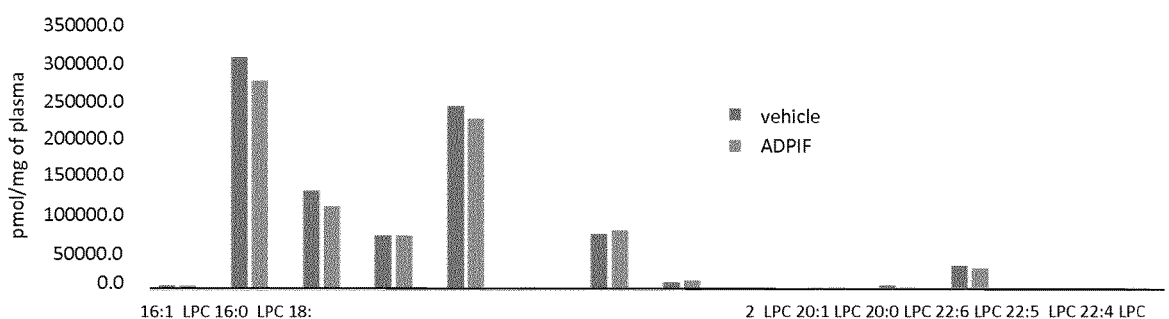

FIGURE 11
DIO vehicle treated
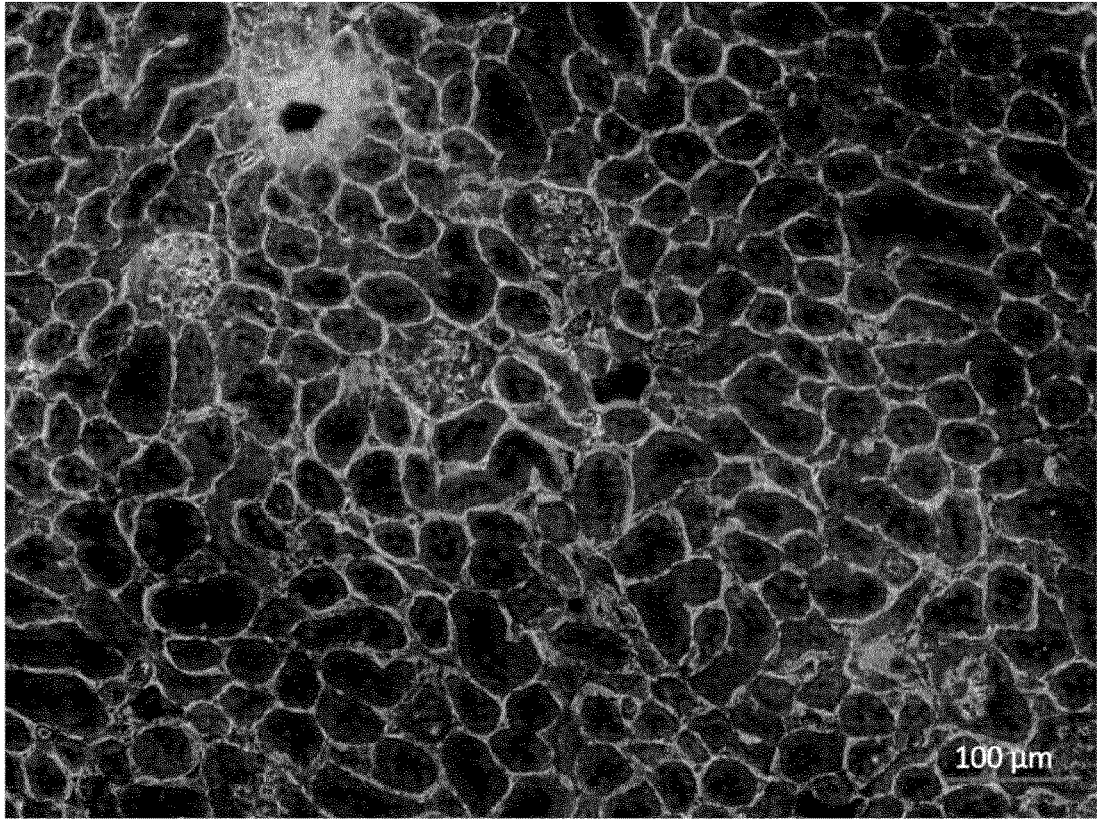
DIO ADPIF treated
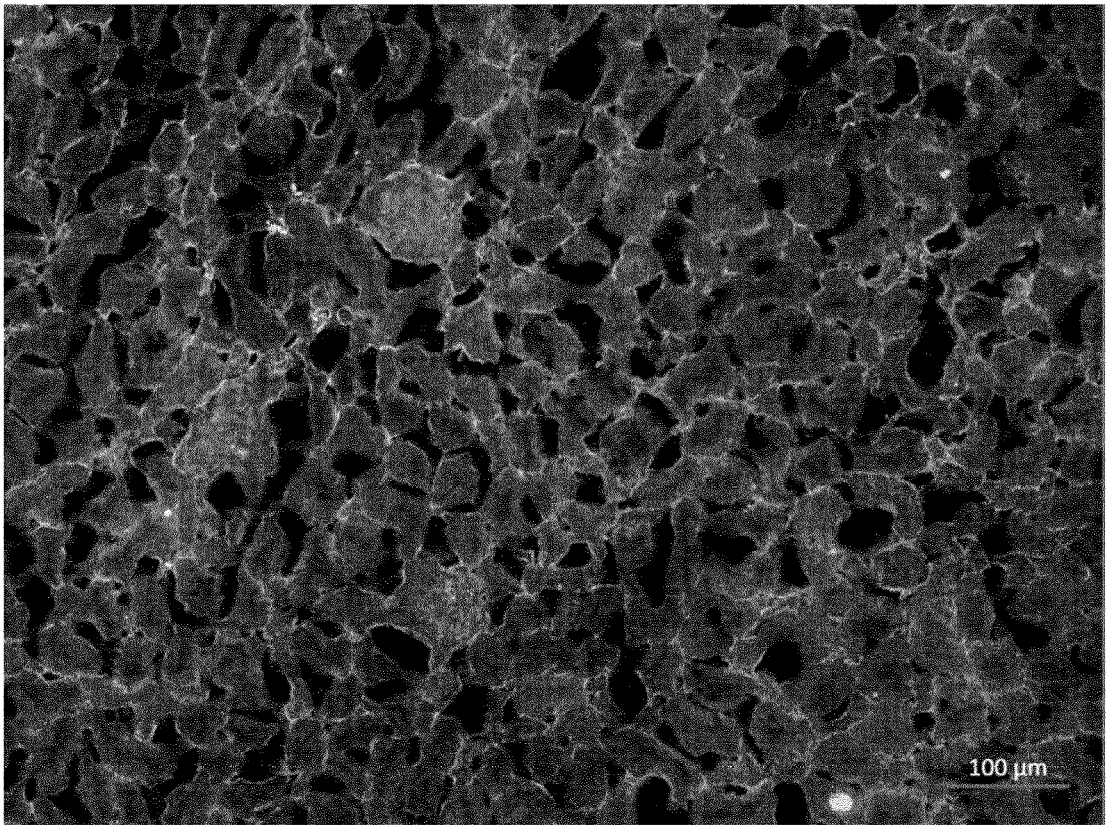

PEPTIDES FOR TREATMENT AND PREVENTION OF NONALCOHOLIC FATTY LIVER DISEASE AND FIBROSIS

CROSS-REFERENCE TO RELATED APPLICATION

This application is the U.S. national stage application of International Patent Application No. PCT/EP2018/085071, filed Dec. 14, 2018.

The Sequence Listing for this application is labeled "Seq-List.txt" which was created on Dec. 14, 2018 and is 25 KB. The entire content of the sequence listing is incorporated herein by reference in its entirety.

FIELD OF THE INVENTION

The present invention relates to the field of the medicine. More particularly, it relates to treatment of liver diseases, in particular hepatic steatosis, especially non-alcoholic steatotic hepatitis and to treatment of fibrosis.

BACKGROUND OF THE INVENTION

NAFLD (nonalcoholic fatty liver disease), defined by the presence of hepatic accumulation of triglycerides in the hepatocytes in absence of any other etiology of liver disease, is the most common cause of chronic liver disease in the Western world. Its clinical-histologic phenotype extends from nonalcoholic fatty liver (NAFL) to nonalcoholic steatohepatitis (NASH), characterized by liver inflammation and progressive fibrosis, leading to cirrhosis and end stage liver disease as well as hepatocellular carcinoma.

Whereas the estimated prevalence of NAFLD ranges from 6 to 33% in the general population, the prevalence of NASH only ranges from 3 to 5%, but NASH-related cirrhosis has become the second leading indication for liver transplantation in the United States. Hospitalizations for NAFLD have increased by 97% since the year 2000.

There are no drugs currently approved to prevent or treat NAFLD or NASH.

Therefore, there is a need for new treatments for preventing or treating nonalcoholic fatty liver disease (NAFLD), non-alcoholic steatohepatitis (NASH), and hepatic steatosis (fatty liver).

Fibrosis is a pathological condition where fibrous connective tissue invades any organ, usually as a consequence of inflammation or other injury. Several compounds are known to treat fibrosis but do so inadequately. Thus, attempts to develop a clinically effective fibrosis have been unsuccessful, and there is still a need to find treatments for fibrosis.

SUMMARY OF THE INVENTION

Surprisingly, the inventors provide peptides from the kinase domain of the PKCα and derivatives thereof which specifically decrease the expression of Solute Carrier Family 27 Member 2 (SLC27A2) commonly known as FATP2 (Fatty acid transport protein 2) in adipose tissue. The peptides are capable, after 3 months of a single injection, of decreasing the phenomenon of steatosis on the liver, in particular capable of decreasing the size of the lipid droplets in the liver, the level of two biomarkers of liver damage (i.e., AST and ALT) and the ratio of liver weight to body weight. In addition, the peptides are capable of decreasing fibrosis, as shown by their capacity to down-regulate de novo lipogenesis pathway (e.g., decrease of ACC (Acetyl-CoA carboxylase) and to decrease LOXL2 hepatic protein content and circulating levels, thereby stopping fibrosis progression. In vivo, a significant decrease of liver triglycerides content and fibrosis area have been observed with a treatment with the peptides, demonstrating an anti-steatotic and anti-fibrosis effect.

Accordingly, the present invention relates to a peptide, wherein
the peptide is capable of decreasing the FATP2 expression in adipose tissue, in particular in a mammal;
the peptide does not simultaneously comprise one methionine, one proline and one arginine;
the peptide adopts a secondary structure which is a helix, preferably an alpha helix; and
the peptide comprises, consists essentially in or consists in a sequence from a segment of at least 5, 6, 7, 8, 9, 10, 11, 12, 13, 14, 15, 16, 17, 18, 19, 20, 21, 22, 23 or 25 consecutive residues of the kinase domain of a PKC (Protein Kinase C) or a segment from 5 to 40 consecutive residues of the kinase domain of a PKC (Protein Kinase C);
the peptide has a length from 5 to 80 amino acids or from 5 to 60 amino acids or from 5 to 40 amino acids, and
the peptide sequence may comprise 1, 2, 3, 4, or 5 modification(s) of an amino acid selected from substitution(s), deletion(s), addition(s), and a mixture thereof within said sequence of a segment of the kinase domain of the PKC.

Preferably, the peptide is modified by a chemical cross-linking process such as stapling. Preferably, the peptide has a length of at least 5 amino acids and less than 40 amino acids, preferably a length of at least 5 amino acids and less than 30 amino acids, more preferably of at least 5 amino acids and less than 25 amino acids.

Preferably, the peptide is capable of decreasing or preventing the interaction between ALMS1 and αPKC.

Optionally, the peptide sequence comprises, consists essentially in or consists in at least one of the following sequences: VECTMVEKRVLA (SEQ ID NO: 3) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKRVLA (SEQ ID NO: 9) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTMVEKXVLA (SEQ ID NO: 10) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKXVLA (SEQ ID NO: 11) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; LDN; SVDWWAYGVLLYEMLA (SEQ ID NO: 6) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; SVDWWAYGVLLYEXLA (SEQ ID NO: 13) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; EDEDELFQSIME (SEQ ID NO: 7) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; EDEDELFQSIXE (SEQ ID NO: 14) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; LDN; AFF; PDY; XDY; PEII (SEQ ID NO: 5); XEII (SEQ ID NO: 18); PAK; XAK; wherein X is any amino acid except M, P and R.

Optionally, the peptide sequence comprises, consists essentially in or consists in at least one of the following sequences: VECTMVEKRVLA (SEQ ID NO: 3) with optionally 1, 2, or 3 modification(s) of an amino acid selected from substitution(s) deletion(s), addition(s), and a mixture thereof; VECTXVEKRVLA (SEQ ID NO: 9) with optionally 1, 2, or 3 modification(s) of an amino acid selected from substitution(s) deletion(s), addition(s), and a mixture thereof; VECTMVEKXVLA (SEQ ID NO: 10) with optionally 1, 2, or 3 modification(s) of an amino acid selected from substitution(s) deletion(s), addition(s), and a mixture thereof; VECTXVEKXVLA (SEQ ID NO: 11) with optionally 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; SVDWWAYGVLLYEMLA (SEQ ID NO: 6) with optionally 1, 2, or 3 modification(s) of an amino acid selected from substitution(s) deletion(s), addition(s), and a mixture thereof; SVDWWAYGVLLYEXLA (SEQ ID NO: 13) with optionally 1, 2, or 3 modification(s) of an amino acid selected from substitution(s) deletion(s), addition(s), and a mixture thereof; EDEDELFQSIME (SEQ ID NO: 7) with optionally 1, 2, or 3 modification(s) of an amino acid selected from substitution(s) deletion(s), addition(s), and a mixture thereof; EDEDELFQSIXE (SEQ ID NO: 14) with optionally 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; wherein X is any amino acid except M, P and R.

Optionally, the peptide sequence comprises, consists essentially in or consists in at least one of the following sequences:

a) VECTXVEKXVLALLDKXXFLTQLHS (SEQ ID NO: 20) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

b) VECTMVEKRVLALLDKXXFLTQLHS (SEQ ID NO: 21) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

c) VECTXVEKRVLALLDKPPFLTQLHS (SEQ ID NO: 22) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

d) VECTMVEKXVLALLDKPPFLTQLHS (SEQ ID NO: 23) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

and the sequence of any segment of at least 5, 6, 7, 8, 9, 10, 11, 12, 13, 14, 15, 16, 17, 18, 19, 20, 21, 22, 23 or 25 consecutive residues of any sequence a) to d).

Optionally, the peptide sequence comprises, consists essentially in or consists in at least one of the following sequences:

VECTMXEKRVLAX (SEQ ID NO: 24)

VECTXXEKRVLAX (SEQ ID NO: 25)

VECTMXEKXVLAX (SEQ ID NO: 26)

VECTXXEKXVLAX (SEQ ID NO: 27)

VECTXXEKXVLAXLDKXXFLTQLHS (SEQ ID NO: 28)

VECTMXEKRVLAXLDKXXFLTQLHS (SEQ ID NO: 29)

VECTXXEKRVLAXLDKPPFLTQLHS (SEQ ID NO: 30)

VECTMXEKXVLAXLDKPPFLTQLHS (SEQ ID NO: 31)

wherein the residues which are bold and underlined X carry the stapling and is any amino acid derivative suitable for stapling; and wherein X is any amino acid except M, P and R, with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

Preferably, said PKC is selected from the group consisting of an alpha-PKC (αPKC), a beta-PKC (βPKC) including βI and βII PKC, delta-PKC, theta-PKC, eta-PKC and epsilon-PKC. More preferably, said PKC is an αPKC of SEQ ID NO: 1.

In a particular embodiment, the peptide sequence comprises, consists essentially in or consists in

VECTTREKEVLASLDKAAFLTQLHS (SEQ ID NO: 32)

wherein R and S carry the stapling, being preferably 2-(7-octenyl)arginine and 2-(4-pentenyl)serine, respectively;

with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

The present invention also relates to a pharmaceutical composition comprising a peptide according to the present disclosure. It also relates to a peptide according to the present disclosure for use as a drug. It further relates to the use of a peptide according to the present disclosure for the manufacture of a drug.

It further relates to a peptide according to the present disclosure or a pharmaceutical composition comprising it for use in the treatment or prevention of a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis.

Optionally, the disease is selected from the group consisting of nonalcoholic fatty liver disease (NAFLD), non-alcoholic fatty liver (NAFL), non-alcoholic steatohepatitis (NASH), and hepatic steatosis (fatty liver). Preferably, the disease is hepatic steatosis (fatty liver) or non-alcoholic steatohepatitis (NASH). More preferably, the disease is non-alcoholic steatohepatitis (NASH).

Optionally, the fibrosis is a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis or a skin fibrosis. Preferably, the fibrosis is a liver fibrosis.

Figure 1A:
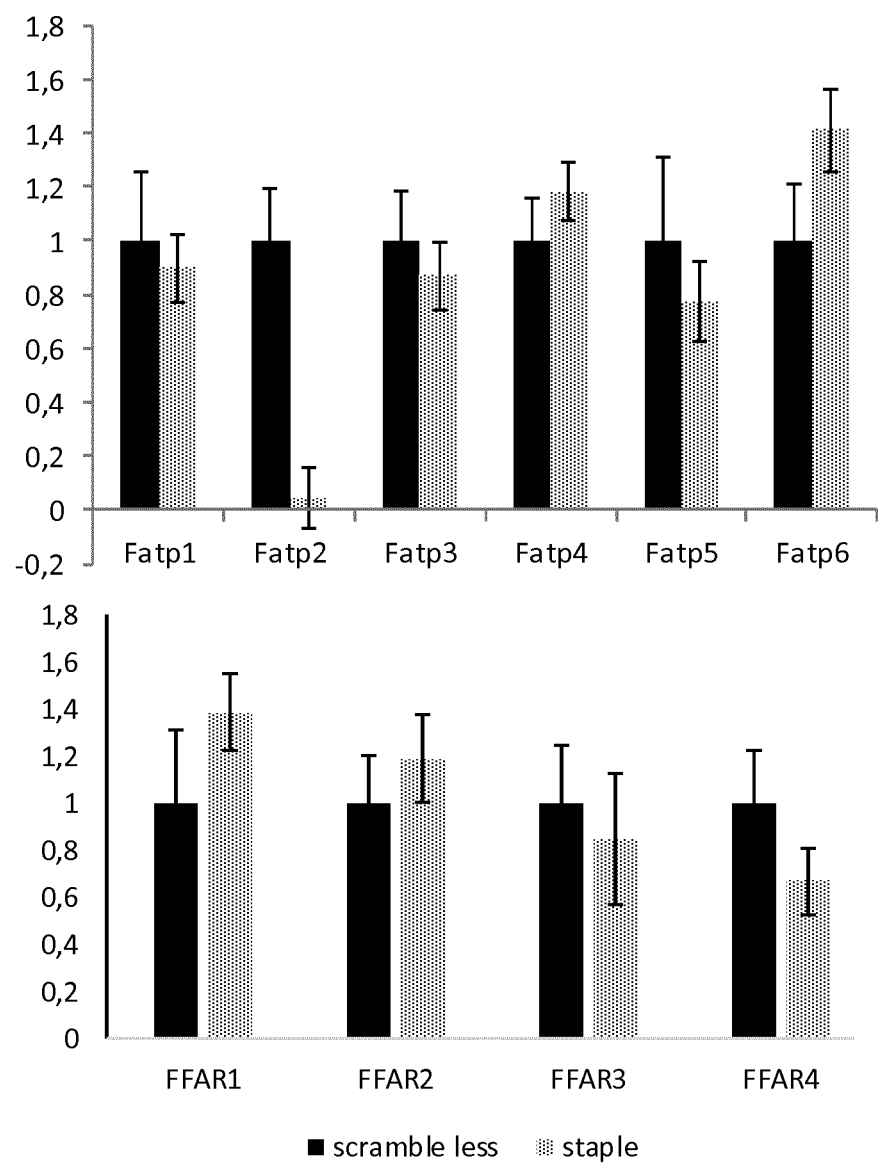
FIG. 1: Effect of adipose tissue targeted PATAD treatment on expression levels of key fatty acids transporters and receptors n=4 animals per group, GAPDH was used as reference gene. There are 6 isoforms of FATP (FATP1-6 also known as SLC27A1-SLC27A6).

Fatp1 (Fatty acid transport protein 1), Fatp2 (Fatty acid transport protein 2), Fatp3 (Fatty acid transport protein 3), Fatp4 (Fatty acid transport protein 4), Fatp5 (Fatty acid transport protein 5), Fatp6 (Fatty acid transport protein 6), FFAR1 (Free Fatty Acid Receptor 1), FFAR2 (Free Fatty Acid Receptor 2), FFAR3 (Free Fatty Acid Receptor 3), FFAR4 (Free Fatty Acid Receptor 4).

"Scramble less" refers to the combination of the two peptides with the same amino acid residues as in the stapled forms but randomly rearranged with a maintained alpha helix structure: Scrambled peptide sequence A and Scrambled peptide sequence B. "Staple" refers to a combination of two stapled peptides: Stapled peptide sequence A and Stapled peptide sequence B.

FIG. 1A depicts the expression levels of the FATPs and FFARs isoforms in the PATAD injected adipose tissue where FATP2 expression level is significantly reduced.

FIGS. 1B and 1C depict the expression levels of the FATPs and FFARs isoforms in the liver and muscle following subcutaneous PATAD injection.

FIG. 2: ADPIF peptide is more active than PATAD peptide in reducing FATP2 expression level in the adipose tissue and in increasing GLP-1 circulating levels (A) 4 month-old male mice fed with a high fat/high glucose diet were used in this set of experiment. Normalized expression levels of FATP2 in the adipose tissue from the different mice 11 days post the indicated condition on the X-axis. n=4 animals per group, GAPDH was used as reference gene;

(B) Circulating concentration of GLP-1 in the same mice 11 days post injection showing that PATAD and ADPIF were able to restore GLP1 circulating levels back to lean controls where scrambled injected mice presented decreased GLP-1 concentrations.

Figure 3A:
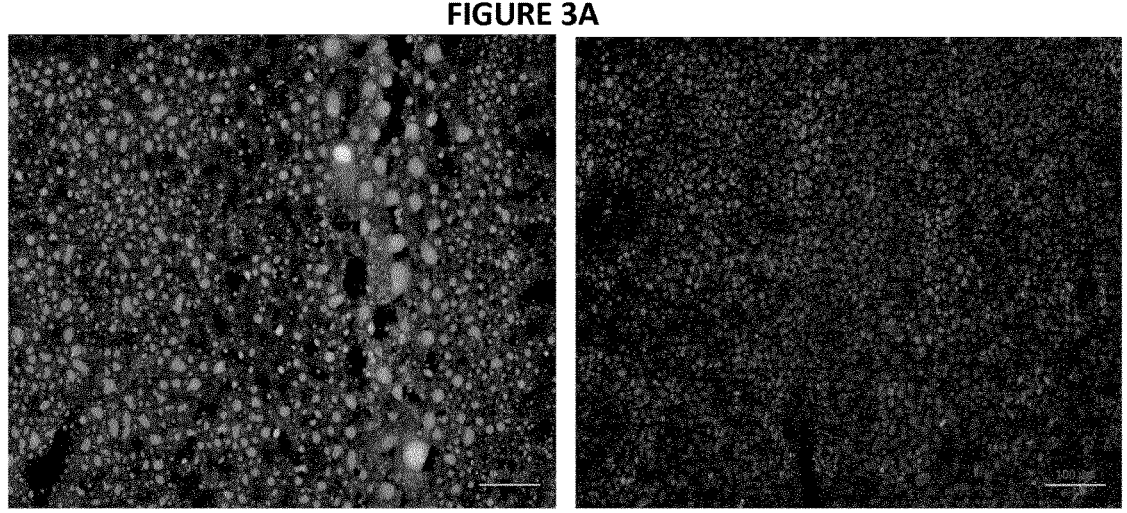
Figure 3B:
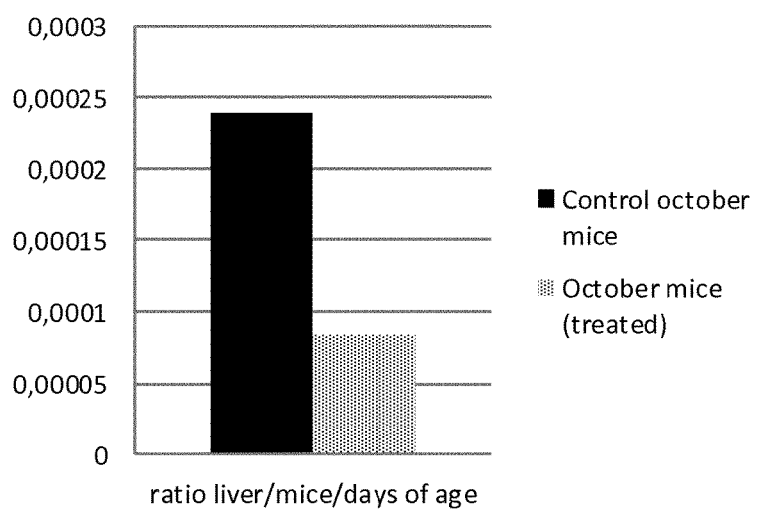

FIG. 3: Effect on liver and circulating aspartate transaminase (AST) and alanine transaminase (ALT) after 3 months of adipose tissue targeted PATAD and ADPIF treatment (A) Fluorescent staining of cryosections from fixated liver from control (left) and PATAD (right) treated mice 3 months after one unique PATAD injection.

(B) Ratio of liver versus body weight times age in days was plotted for n=1 animal per group for PATAD peptide.

(C)-(D) Mean values of both AST (FIG. 3C) and ALT (FIG. 3D) measured by ELISA approach in plasma of mice with the indicated treatment. n=4 samples per group.

PATAD and ADPIF are both effective in reducing circulating levels of AST and ALT. ADPIF is more active in reducing circulating levels of ALT, which translates improvement of liver cell injury.

Figure 4A:
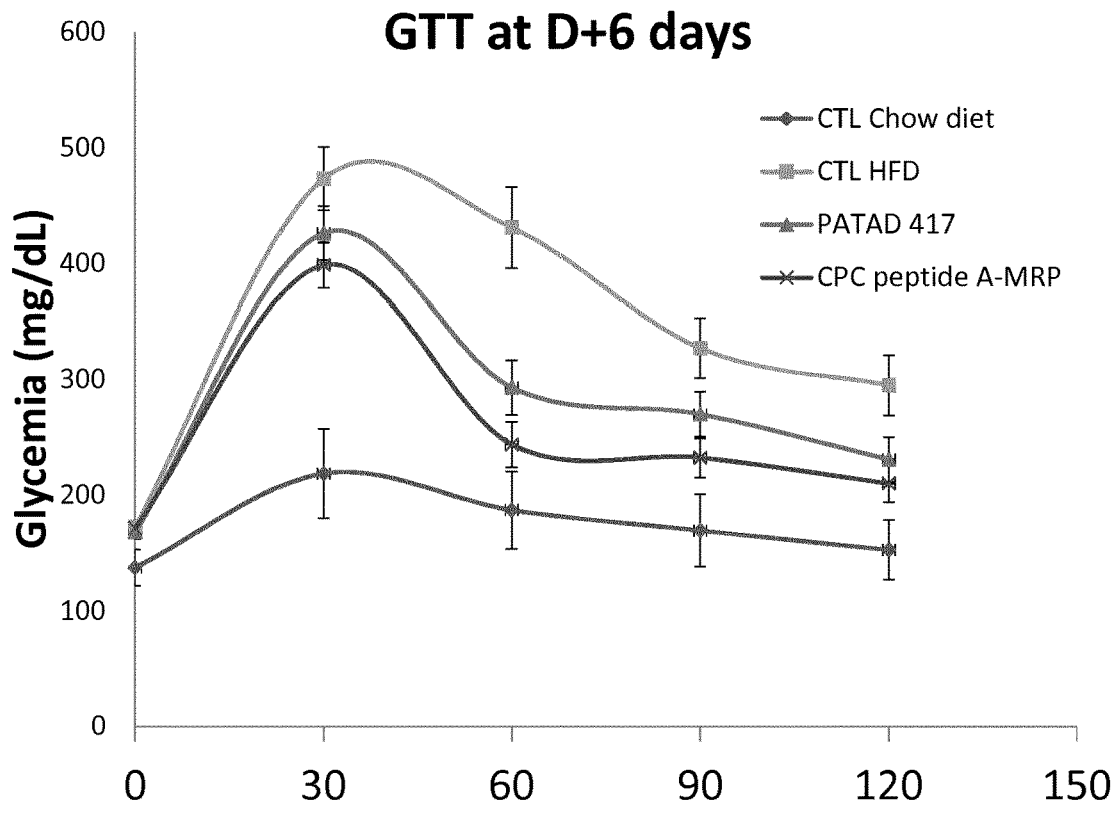
Figure 4B:
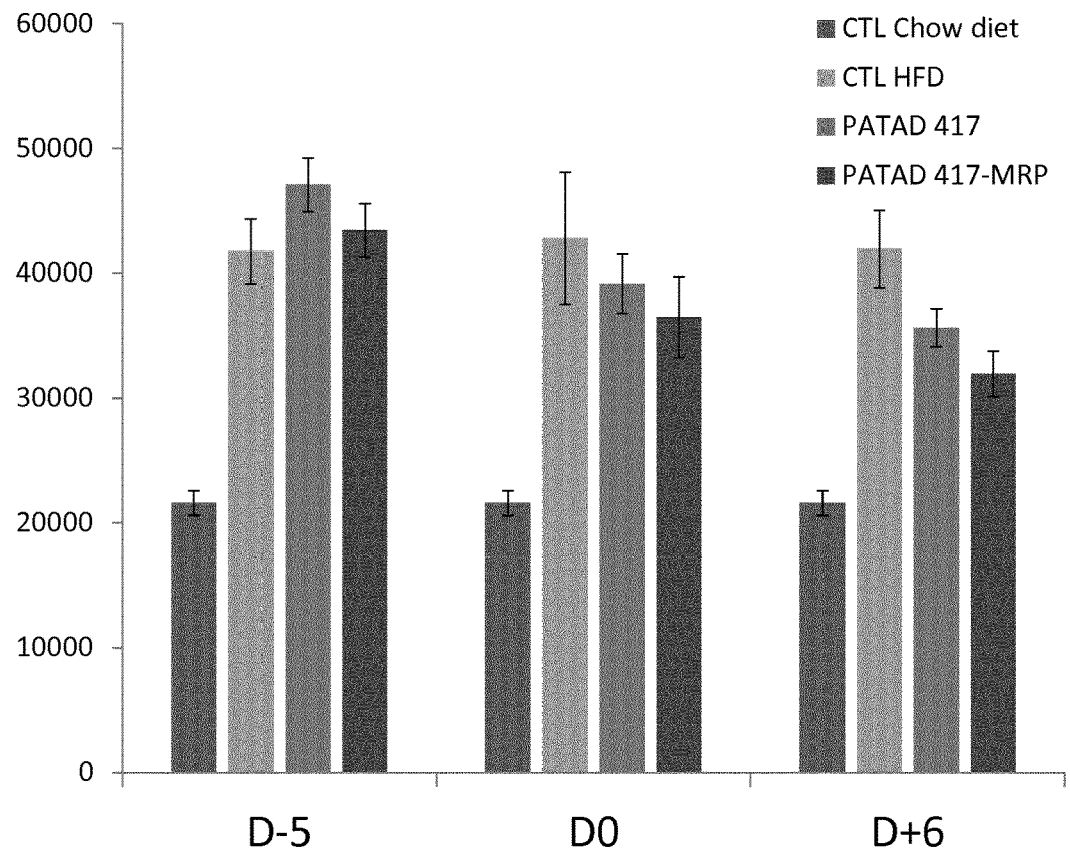

FIG. 4. ADPIF peptide is more active than PATAD peptide in preventing hyperglycemia (A) Time point series in days at 30 minutes glucose bolus in fasting male diet induced obese (DIO) (CTL HFD) and controls (CTL Chow diet) after a single injection of the PATAD (PATAD 417) or ADPIF (CPC peptide A-MRP) treatment at day 0. The glucose bolus is injected subcutaneously which by-passes the liver and goes directly in the blood stream.

(B) Effect on glucose tolerance in fasting male diet induced obese (DIO) (CTL HFD) and controls (CTL Chow diet) by measure of the area under the curve before (D-5) at the moment of treatment and after (D+6) treatment with PATAD (PATAD 417) and ADPIF (PATAD 417-MRP) peptides.

FIG. 5. ADPIF is more active than PATAD in decreasing hepatic protein content of lysyl oxidase like 2 protein (LOXL2) and fatty acid binding protein 4 (FABP4) in DIO male mice.

(A) LOXL2 is a known key actor for fibrosis progression. ELISA results measuring LOXL2 on liver extracts 3 months post vehicle, PATAD or ADPIF injection in the subcutaneous adipose tissue. A significant decrease in hepatic protein content is observed after either PATAD or ADPIF treatment with ADPIF being the most effective peptide. n=4 mice per group.

(B) FABP4 is a key actor of lipid-mediated processes in the cell and is elevated in the liver associated with NAFLD. We measured the FABP4 protein content 3 months after either scramble or PATAD or ADPIF single injection. FABP4 is significantly reduced following either PATAD or ADPIF injection, with ADPIF being more active than PATAD.

FIG. 6. Effect of ADPIF on ceramides in the liver content and profile. Ceramides are a group of biological active lipids known to be involved in NAFLD. We measured and determined the effect of ADPIF injections on the ceramides profile following 3 injections of ADPIF at a frequency of one injection per week in the subcutaneous adipose tissue. ADPIF globally induces a decrease in the hepatic ceramides content with variations between the different ceramides.

FIG. 7. Effect on the liver triglycerides content after 3 months of adipose tissue targeted ADPIF treatment.

Fluorescent staining of cryosections from fixated liver from control (left) and ADPIF (right) treated mice 3 months after one unique ADPIF injection showing a decrease in the diameter of the lipid droplets indicating an overall decrease in total triglycerides in the liver. Mice were DIO male mice age 7 months at the end of the experiment.

Figure 8:
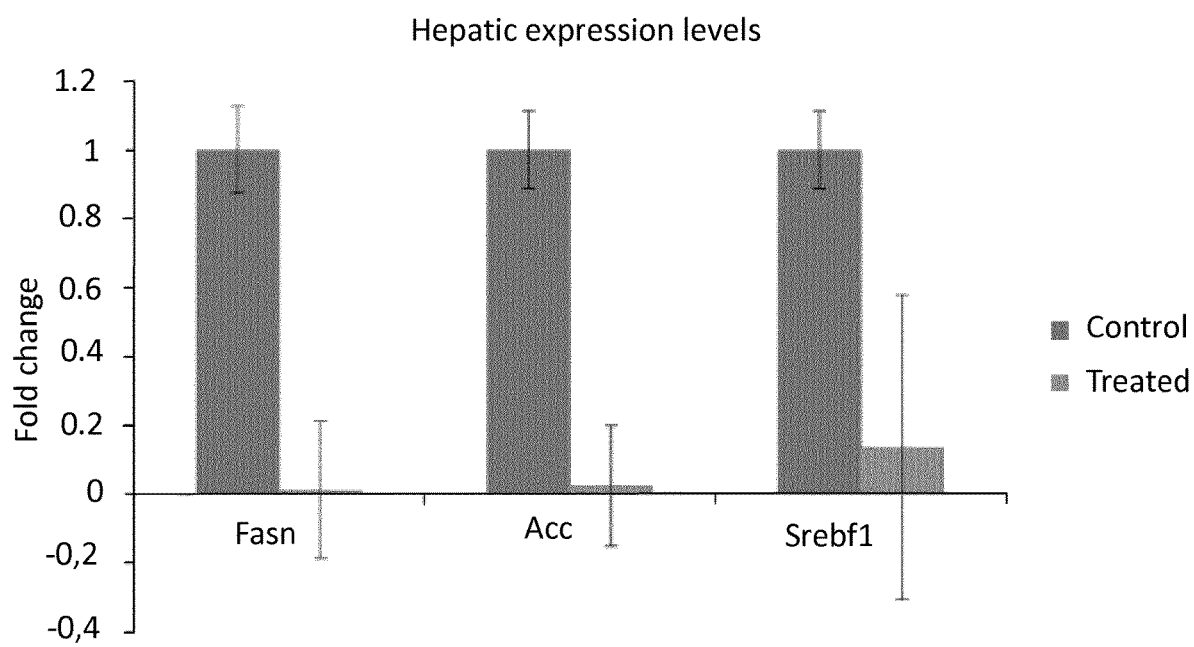

FIG. 8. ADPIF peptide treatment downregulates de novo lipogenesis pathway genes after 11 days in DIO male mice. 11-day post ADPIF peptide injection in the adipose tissue, hepatic expression levels of fatty acid synthase (Fasn), Acetyl-CoA carboxylase (Acc) and Sterol regulatory element binding transcription factor 1 (Srebf1) were significantly decreased compared to control indicating that the de novo lipogenesis in the liver of ADPIF-treated mice was shut down.

FIG. 9. ADPIF treatment reduces fibrotic lesions in the liver.

(A) Immunostaining pictures of cryosections from liver of DIO-NASH untreated and DIO-NASH treated with ADPIF, 3 months after ADPIF injection in the subcutaneous adipose tissue. Collagen IV and LOXL2 is highly expressed in the DIO-NASH untreated and reduced in the DIO-NASH ADPIF treated.

(B) As LOXL2 is also secreted, we measured the effect of ADPIF on the circulation levels of LOXL2 and found that ADPIF treatment (3 months post a unique injection) reduced the LOXL2 levels by half.

(C) Liver sections were analyzed by transmitted electron microscopy to identify the fibrotic depots in the DIO-NASH untreated liver. No such fibrotic depots were found in the DIO-NASH treated liver 3 months after ADPIF injection in the subcutaneous adipose tissue.

FIG. 10. ADPIF treatment impact on lysophosphatidylcholines (LPC) lipids. Lysophosphatidylcholines (LPCs) are substrates for a pro-fibrotic enzymes, Autotaxin which is a key enzyme in the generation of lysophosphatidic acid. The latter is a bioactive lipid known to be playing a role in fibrotic progression that affect the liver but also the kidney and other soft tissues. We therefore measured the level of the different (LPCs) in pancreas (A), adipose tissue (B), liver (C) and plasma (D).

ADPIF treatment (given at a frequency of one subcutaneous injection of 25 µg per mouse for a period of 3 weeks and then the mice were euthanized after 1 week after the last injection), induces a selective decrease of certain LPCs in the different tissues analyzed. LPC 18:2 is the lipid which is the mostly reduced following ADPIF treatment both in the pancreas, adipose tissue and liver.

FIG. 11. ADPIF peptide protects the kidney from fibrosis Cryosections from kidneys of DIO-NASH treated with vehicle and DIO-NASH ADPIF treated were immunostained for Collagen IV, ZO-1 and the nuclei. More depots of Collagen IV are observed in the DIO-NASH vehicle than in the ADPIF treated.

DETAILED DESCRIPTION OF THE INVENTION

Surprisingly, the inventors provide peptides from the kinase domain of the PKCα and derivatives thereof which specifically decrease the expression of FATP2 (Fatty acid transport protein 2) in adipose tissue (FIG. 1A). The peptides are capable, after 3 months of a single injection, of decreasing the phenomenon of steatosis on the liver, in particular capable of decreasing the size of the lipid droplets in the liver, the level of two biomarkers of liver damage (i.e., AST and ALT) and the ratio of liver weight to body weight (FIG. 3). In addition, the peptides are capable of decreasing fibrosis, as shown by their capacity to down-regulate de novo lipogenesis pathway (e.g., decrease of ACC (Acetyl-CoA carboxylase) (FIG. 8) and to decrease the protein level of LOXL2 in the liver and in circulation (FIGS. 5 and 9A), thereby stopping fibrosis progression. The peptides are also capable of decreasing collagen deposit in the kidney. In vivo, a significant decrease of fibrosis area has been observed with a treatment with the peptides, demonstrating an anti-fibrosis effect. Accordingly, the invention relates to a peptide as defined herein;

a pharmaceutical composition comprising a peptide as defined herein;

a peptide as defined herein for use as a drug or the use of a peptide as defined herein for the manufacture of a drug;

a peptide or a pharmaceutical composition comprising the peptide for use in the treatment or prevention of a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

the use of a peptide for the manufacture of a medicine for the treatment or prevention of a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

a method for the treatment or prevention of a disease in a subject, comprising administering a therapeutically effective amount of a peptide, wherein the disease is selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis.

Definitions

ALMS1, Alström syndrome protein 1, is a protein encoded by the ALMS1 gene. Mutations in the ALMS1 gene have been found to be causative for Alström syndrome. It is described in several databases, namely UniProt ID No Q8TCU4; Gene ID No 7840, HGNG ID No 428. Reference sequences are disclosed in Genbank under NM_015120.4 for mRNA and NP_055935.4 for protein.

The terms "Protein kinase C" and "PKC" (EC 2.7.11.13) are equivalent and refers to a family of protein kinase enzymes that are involved in controlling the function of other proteins through the phosphorylation of hydroxyl groups of serine and threonine amino acid residues on these proteins. PKC are typically activated by signals such as increases in the concentration of diacylglycerol (DAG) or calcium ions (Ca2+). PKC play important roles in several signal transduction cascades.

The PKC family comprises at least fifteen isozymes in humans, divided into three main subfamilies, conventional (or classical) PKCs, novel PKCs, and atypical PKCs.

Conventional (c)PKCs comprises the isoforms α, βI, βII, and γ. These PKCs require $Ca^{2+}$, DAG, and a phospholipid such as phosphatidylserine for activation.

Novel (n)PKCs include the δ, ε, η, and θ isoforms. These PKCs require DAG, but do not require Ca2+ for activation.

Atypical (a)PKCs include the ζ, ι, and λ, isoforms. These PKCs require neither Ca2+ nor diacylglycerol for activation.

Protein kinase C alpha type, also called αPKC, PKC-A or PKC-alpha, belongs to a family of serine- and threonine-specific protein kinases that can be activated by calcium and the second messenger diacylglycerol. It is described in several databases, namely UniProt ID No P17252, Gene ID No 9393, HGNG ID No 5578. Reference sequences are disclosed in Genbank under NM_02737.2 for mRNA and NP_002728.1 for protein. The protein sequence of human αPKC is disclosed in SEQ ID NO: 1.

The kinase domain of the αPKC is from position 339 to position 595 as disclosed in SEQ ID NO: 1 and is shown in SEQ ID NO: 2.

"consists of," "consists essentially of" or "substantially comprises": The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context. For instance, a peptide or protein described herein as comprising a particular sequence should be understood as also describing a peptide or protein consisting of that sequence, unless otherwise stated or clearly contradicted by context. By "consists essentially of" is intended that the peptide or protein consists of that sequence, but it may also include 1, 2, 3, 4, 5, 6, 7, 8, 9 or 10 substitutions, additions, deletions or a mixture thereof, preferably 1, 2, 3, 4, or 5 substitutions, additions, deletions or a mixture thereof. In particular, by "essentially consist in", it may be intended that the peptide may include 1, 2, 3, 4, 5, 6, 7, 8, 9 or 10 additional amino acids at the N and/or C-terminal end, preferably 1, 2, 3, 4, or 5 additional amino acids, and/or 1, 2 or 3 substitutions, deletions, additions, or a mixture thereof. Preferably, the number of substitutions, additions, deletions or a mixture thereof depends on the length of the sequence. For instance, the percentage of substitutions, deletions, additions, or a mixture thereof may be no more than 30%, preferably no more than 25%.

As used herein, the term "substitution" refers to the exchange of a single amino-acid by another in a peptide sequence.

As used herein, the term "deletion" refers to the removal of a single amino-acid in a peptide sequence.

As used herein, the term "insertion" or "addition" are equivalent and refer to the addition of a single amino-acid in a peptide sequence.

By "substitutions, additions, deletions" is intended a substitution, addition, deletion of one amino acid. Then, when it is referred to "1, 2, 3, 4, 5, 6, 7, 8, 9 or 10 substitutions, additions, deletions or a mixture thereof", "1, 2, 3, 4, or 5 substitutions, additions, deletions or a mixture thereof" or "1, 2 or 3 substitutions, deletions, additions, or a mixture thereof", it means respectively "1, 2, 3, 4, 5, 6, 7, 8, 9 or 10 modification(s) of an amino acid selected from substitutions, additions, deletions and a mixture thereof", "1, 2, 3, 4, or 5 modification(s) of an amino acid selected from substitutions, additions, deletions or a mixture thereof" or "1, 2 or 3 modification(s) of an amino acid selected from substitutions, deletions, additions, or a mixture thereof". "1, 2, 3, 4, or 5 substitutions, additions, deletions or a mixture thereof" also means "from 1 to 5 substitutions, additions, deletions or a mixture thereof". "1, 2, or 3 substitutions, additions, deletions or a mixture thereof" also means "from 1 to 3 substitutions, additions, deletions or a mixture thereof".

In the peptide sequences disclosed herein, the amino acids are represented by their one letter code according to the following nomenclature: A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophane and Y: tyrosine.

As used herein, the terms "sequence identity" or "identity" refers to an exact amino acid to amino acid correspondence of two peptides. Percent of identity can be determined by a direct comparison of the sequence information between two molecules by aligning the sequences, counting the exact number of matches between the two aligned sequences, dividing by the length of the shorter sequence, and multiplying the result by 100.

The sequence identity can be determined by alignment of two peptide sequences using global or local alignment algorithms, depending on the length of the two sequences. Sequences of similar lengths are preferably aligned using global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity. GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths.

By "increased", "increase" or "enhance" is intended to refer to a measurement increased by at least 10, 20, 30, 40, 50, 60, 70, 80 or 90% when compared to the measurement measured in absence of the tested molecule in the same conditions. By "decreased" or "decrease" is intended to refer to a measurement decreased by at least 10, 20, 30, 40, 50, 60, 70, 80 or 90% when compared to the measurement measured in absence of the tested molecule in the same conditions.

As used herein, the term "treatment", "treat" or "treating" refers to any act intended to ameliorate the health status of patients, such as cure, alleviate or delay of the disease. It includes preventive as well as therapeutic treatment. For instance, it may refer to a delay or a blockade of the evolution from NAFLD to NASH, from NASH to NASH with fibrosis, from NASH to cirrhosis, from NASH or cirrhosis to hepatocellular carcinoma. The term treatment designates in particular the correction, retardation, or reduction of the hepatic steatosis. The term "treatment" also designates an improvement in the liver steatosis, in liver inflammation, in liver fibrosis, in liver enzymes (aminotransferases such as AST and ALT), and/or in fatty liver index (Bedgni et al, BMC Gastroenterol. 2006 Nov. 2; 6:33). In particular, the treatment lowers or decreases or delays the in the liver steatosis, in liver inflammation, in liver fibrosis, in liver enzymes (aminotransferases such as AST and ALT), and/or in fatty liver index. In the context of fibrosis, it may refer to a delay or a blockade of the evolution of fibrosis. In particular, the term treatment designates in particular the correction, retardation, or reduction of fibrosis.

As used herein, the term "effective amount" refers to a quantity of a peptide of the present disclosure or of a pharmaceutical composition of the present disclosure which treats or delays the progression or onset of nonalcoholic fatty liver disease (NAFLD), non-alcoholic fatty liver (NAFL), non-alcoholic steatohepatitis (NASH), hepatic steatosis (fatty liver), liver fibrosis, liver inflammation, cirrhosis, or hepatocellular carcinoma. It can also refer to a quantity of a peptide of the present disclosure or of a pharmaceutical composition of the present disclosure which treats or delays fibrosis.

As used herein, the terms "active principle", "active ingredient" and "active pharmaceutical ingredient" are equivalent and refers to a component of a pharmaceutical composition having a therapeutic effect.

As used herein, the term "therapeutic effect" refers to an effect induced by an active ingredient, such as a peptide of the present disclosure, or by a pharmaceutical composition according to the present disclosure, capable to treat or to delay the progression or onset of a disease such as nonalcoholic fatty liver disease (NAFLD), non-alcoholic fatty liver (NAFL), non-alcoholic steatohepatitis (NASH), hepatic steatosis (fatty liver), liver fibrosis, liver inflammation, cirrhosis, hepatocellular carcinoma or fibrosis.

As used herein, the term "excipient or pharmaceutically acceptable carrier" refers to any ingredient except active ingredients that is present in a pharmaceutical composition. Its addition may be aimed to confer a particular consistency or other physical or gustative properties to the final product. An excipient or pharmaceutically acceptable carrier must be devoid of any interaction, in particular chemical, with the actives ingredients.

As used herein, the terms "subject", "individual" or "patient" are interchangeable and refer to an animal, preferably to a mammal, even more preferably to a human, including adult, child, newborn and human at the prenatal stage.

In the present document, the term "about" refers to a range of values of ±10% of the specified value. For example, "about 50" comprise values of ±10% of 50, i.e. values in the range between 45 and 55. Preferably, the term "about" refers to a range of values of ±5% of the specified value.

As used herein, "nonalcoholic fatty liver disease" and "NAFLD" refer to a disease defined by the presence of macrovascular steatosis in the presence of less than 20 g of alcohol ingestion per day. NAFLD is the most common liver disease in the United States, and is commonly associated with insulin resistance/type 2 diabetes mellitus and obesity. NAFLD is manifested by steatosis, steatohepatitis, cirrhosis, and sometimes hepatocellular carcinoma. For a review of NAFLD, see Tolman and Dalpiaz (2007) Ther. Clin. Risk.

Manag., 3(6): 1153-1163 the entire contents of which are incorporated herein by reference.

As used herein, the terms "steatosis," "hepatic steatosis," and "fatty liver" refer to the accumulation of triglycerides and other fats in the liver cells.

As used herein, the term "Nonalcoholic steatohepatitis" or "NASH" refers to liver inflammation and damage caused by a buildup of fat in the liver. NASH is part of a group of conditions called nonalcoholic fatty liver disease (NAFLD). NASH resembles alcoholic liver disease, but occurs in people who drink little or no alcohol. The major feature in NASH is fat in the liver, along with inflammation and damage. Most people with NASH feel well and are not aware that they have a liver problem. Nevertheless, NASH can be severe and can lead to cirrhosis, in which the liver is permanently damaged and scarred and no longer able to work properly. NASH is usually first suspected in a person who is found to have elevations in liver tests that are included in routine blood test panels, such as alanine aminotransferase (ALT) or aspartate aminotransferase (AST). When further evaluation shows no apparent reason for liver disease (such as medications, viral hepatitis, or excessive use of alcohol) and when x rays or imaging studies of the liver show fat, NASH is suspected. The only means of proving a diagnosis of NASH and separating it from simple fatty liver is a liver biopsy.

As used herein, the term "cirrhosis," defined histologically, is a diffuse hepatic process characterized by fibrosis and conversion of the normal liver architecture into structurally abnormal nodules.

NAFLD may be differentiated from NASH by the NAFLD Activity Score (NAS), the sum of the histopathology scores of a liver biopsy for steatosis (0 to 3), lobular inflammation (0 to 2), and hepatocellular ballooning (0 to 2). A NAS of <3 corresponds to NAFLD, 3-4 corresponds to borderline NASH, and >5 corresponds to NASH. The biopsy is also scored for fibrosis (0 to 4).

Peptides

The peptide(s) according to the present disclosure present (s) the following features:
  it does not simultaneously comprise one methionine, one proline and one arginine;
  preferably, it adopts a secondary structure which is a helix, preferably an alpha helix;
  it comprises, consists essentially in or consists in a sequence from a segment of the kinase domain of a PKC (Protein Kinase C), preferably a segment of at least 5, 6, 7, 8, 9, 10, 11, 12, 13, 14, 15, 16, 17, 18, 19, 20, 21, 22, 23 or 25 consecutive residues of the kinase domain of a PKC (Protein Kinase C); and
  the peptide sequence may comprise 1, 2, 3, 4, or 5 amino acid modification(s) selected from substitution(s), deletion(s), addition(s), and a mixture thereof within said sequence of a segment of the kinase domain of the PKC.

The peptide(s) may further present one or several of the following features:
  it has a length of less than 80 amino acids, more preferably less than 60 amino acids, still preferably less than 40 amino acids, and even more preferably less than 30 amino acids;
  it has a length of at least 5 amino acids and less than 40 amino acids, preferably a length of at least 5 amino acids and less than 30 amino acids, more preferably of at least 5 amino acids and less than 25 amino acids;
  it is modified by a cross-link;
  it is able to interfere with ALMS1-PKC interaction, in particular to decrease or prevent the interaction between ALMS1 and αPKC; or it is not able to interfere with ALMS1-PKC interaction, in particular to decrease or prevent the interaction between ALMS1 and αPKC;
  it modifies the expression levels of the FATPs expression in adipose tissue, preferentially it decreases the FATP2 expression in adipose tissue;
  it decreases the liver steatosis, the amount of fat in liver, the size of fat droplets in liver, and/or the fatty liver index;
  it induces the expression levels of heme oxygenase 1 in the adipocytes.

The peptide(s) may further present one or several of the following features:
  it has a length of less than 80 amino acids, more preferably less than 60 amino acids, still preferably less than 40 amino acids, and even more preferably less than 30 amino acids;
  it has a length of at least 5 amino acids and less than 40 amino acids, preferably a length of at least 5 amino acids and less than 30 amino acids, more preferably of at least 5 amino acids and less than 25 amino acids;
  it is modified by a cross-link;
  it is not able to interfere with ALMS1-PKC interaction, in particular to decrease or prevent the interaction between ALMS1 and αPKC;
  it modifies the expression levels of the expression of collagen IV and LOXL2 (Lysyl oxidase homolog 2), preferentially it decreases the expression of collagen IV and LOXL2, in particular the LOXL2 expression in liver and/or plasma;
  it decreases the fibrosis;
  It is capable of decreasing the lysophosphatidylcholine (LPC) lipid content in the tissues and in circulation, preferentially the 18:2 LPC.

In one aspect, the peptide of the present disclosure comprises, consists essentially in or consists in a sequence from a segment of the kinase domain of a PKC (Protein Kinase C). The PKC can be selected from conventional PKC, novel PKC and atypical PKC. In particular, the PKC can be selected from conventional PKC. Preferably, the PKC can be selected from the group consisting of α, βI, βII and γ PKCs. More preferably, the PKC can be selected from the group consisting of α, βI, and βII PKCs. Even more preferably, the PKC is an α PKC, preferably a human α PKC, more preferably a human αPKC of SEQ ID NO: 1. The kinase domain of the human αPKC is disclosed in SEQ ID NO: 2.

The segment of the kinase domain of a PKC has at least 5, 6, 7, 8, 9, 10, 11, 12, 13, 14, 15, 16, 17, 18, 19, 20, 21, 22, 23 or 25 consecutive residues of the kinase domain of a PKC. In one aspect, the segment of the kinase domain of a PKC has from 5 to 40 consecutive residues of the kinase domain of a PKC (optionally, from 5 to 30 or from 5 to 25 or from 7 to 25 or from 8 to 25 or from 9 to 25 or from 10 to 25 or from 11 to 25 or from 12 to 25).

The kinase domain of PKC from which the segment is selected has preferably at least 40% of identity with the sequence of SEQ ID NO: 2, more preferably at least 45, 50, 55, 60, 65, 70, 75, 80, 85, 90 or 95% of identity with the sequence of SEQ ID NO: 2.

Preferably, said sequence of a segment of the kinase domain of a PKC corresponds to at least 10%, 20%, 30%, 40%, 50%, 60%, 70%, 80%, 90%, 95%, 99% of the sequence of the peptide. In a particular embodiment, the peptide sequence according to the present disclosure consist in the sequence of a segment of SEQ ID NO: 1.

When the segment of the kinase domain of a PKC comprises one methionine and/or one proline and/or one arginine, then the sequence can be modified (i.e., by introducing substitution(s)) so as to remove all the proline residues, and/or all the methionine residues, and/or all the arginine residues. For instance, the sequence can be modified (i.e., by introducing substitution(s)) so as to remove all the proline residues. Alternatively, the sequence can be modified (i.e., by introducing substitution(s)) so as to remove all the methionine residues. Otherwise, the sequence can be modified (i.e., by introducing substitution(s)) so as to remove all the arginine residues. In one aspect, the sequence can be modified (i.e., by introducing substitution(s)) so as to remove all the proline and methionine residues. In another aspect, the sequence can be modified (i.e., by introducing substitution(s)) so as to remove all the proline and arginine residues. In an additional aspect, the sequence can be modified (i.e., by introducing substitution(s)) so as to remove all the methionine and arginine residues. More preferably, the sequence can be modified (i.e., by introducing substitution(s)) so as to remove all the proline residues, all the methionine residues, and all the arginine residues.

Preferably, the peptide comprises no more than 20, preferably no more than 15, more preferably no more than 10, amino acid modifications selected from substitutions, deletions, additions, and a mixture thereof. In a particularly preferred embodiment, the peptide may comprise 1, 2, 3, 4, 5, 6, 7, 8, 9 or 10 amino acid modifications selected from substitution(s), deletion(s), addition(s), and a mixture thereof, preferably 1, 2, 3, 4, or 5, more preferably 1, 2 or 3.

For instance, the peptide has at least 70%, 75%, 80%, 85%, 90%, 95%, 99% of identity with the sequence of a segment of the kinase domain PKC, preferably of SEQ ID NO: 2. In one embodiment, the part of the sequence of the peptide corresponding to SEQ ID NO: 2 has at least 70%, 75%, 80%, 85%, 90%, 95%, of identity with the sequence of a segment of SEQ ID NO: 2.

For instance, the sequence of a segment of the kinase domain of the PKC may belong to the sequences between positions 339 and 432 of SEQ ID NO: 1, between positions 434 and 544 of SEQ ID NO: 1, between positions 546 and 561 of SEQ ID NO: 1, between positions 563 and 565 of SEQ ID NO: 1, or between positions 568 and 595 of SEQ ID NO: 1.

In one embodiment, the sequence of a segment of the kinase domain of PKC may not include the following residues: G433, E545, S562, S566 of SEQ ID NO: 1.

In one aspect, the peptide of the present disclosure has an alpha helix structure. As used herein, the terms "alpha helix" "α-helix", "classic Pauling-Corey-Branson α-helix" and "3.613-helix" are equivalent and refer to each other. The term "alpha helix" refers to a common motif in the secondary structure of proteins which is a right hand-coiled or spiral conformation (helix) in which every backbone N—H group donates a hydrogen bond to the backbone C=O group of the amino acid located three or four residues earlier along the protein sequence. An alpha helix has an average number of residues per helical turn of about 3.6 residues and 13 atoms are involved in the ring formed by the hydrogen bond.

In a particular embodiment, the peptide of the present disclosure has an alpha helix structure and/or has a sequence which is predictive of an alpha helix structure. Methods to determine the structure of a peptide are well known from the man skilled in the art, such as Circular Dichroism or NMR. Likewise, methods to predict an alpha helix structure of a peptide are well known from the man skilled in the art such as STRIDE (Frishman D., Argos P., Proteins, vol. 23, no 4, 1995, p. 566-579); DEFINE (Richards F. M., Kundrot C. E., Proteins, vol. 3, no 2, 1988, p. 71-84); DSSP (Touw et al. Nucleic Acids Research 2015; 43: D364-D368; Kabsch & Sander. Biopolymers. 1983, 22, 2577-2637).

The alpha helices are located in the kinase domain at the following locations: 372-377; 381-392; 425-432; 437-456; 466-468; 502-504; 507-510; 518-533; 543-552; 563-572; 577-579; 587-593 and 595-597 of SEQ ID NO: 1.

According, the peptide may comprise, consist essentially in or consist in at least one of the following sequences:

```
                                  (SEQ ID NO: 3)
          VECTMVEKRVLA;

(SEQ ID NO: 4)
          LMYHIQQV;

LDN;

PDY;

(SEQ ID NO: 5)
          PEII;

(SEQ ID NO: 6)
          SVDWWAYGVLLYEMLA;

(SEQ ID NO: 7)
          EDEDELFQSIME;

PAK;

(SEQ ID NO: 8)
          GERDVRE;

AFF.
```

In a particular embodiment, the peptide may comprise, consist essentially in or consist in at least one of the following sequences:

```
                                  (SEQ ID NO: 3)
          VECTMVEKRVLA;
          and
                                  (SEQ ID NO: 8)
          GERDVRE.
```

Optionally, the peptide may comprise, consist essentially in or consist in at least one of the following sequences: VECTMVEKRVLA (SEQ ID NO: 3); VECTXVEKRVLA (SEQ ID NO: 9); VECTMVEKXVLA (SEQ ID NO: 10); VECTXVEKXVLA (SEQ ID NO: 11); LMYHIQQV (SEQ ID NO: 4); LXYHIQQV (SEQ ID NO: 12); LDN; SVDWWAYGVLLYEMLA (SEQ ID NO: 6); SVDWWAYGVLLYEXLA (SEQ ID NO: 13); EDEDELFQSIME (SEQ ID NO: 7); EDEDELFQSIXE (SEQ ID NO: 14); GERDVRE (SEQ ID NO: 8); GEXDVRE (SEQ ID NO: 15); GERDVXE (SEQ ID NO: 16); GEXDVXE (SEQ ID NO: 17); LDN; AFF; PDY; XDY; PEII (SEQ ID NO: 5); XEII (SEQ ID NO: 18); PAK; XAK; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y. In one aspect, the peptide may comprise, consist essentially in or consist in at least one of the following sequences: VECTMVEKRVLA (SEQ ID NO: 3); VECTXVEKRVLA (SEQ ID NO: 9); VECTMVEKXVLA (SEQ ID NO: 10); VECTXVEKXVLA (SEQ ID NO: 11); LMYHIQQV (SEQ ID NO: 4); LXYHIQQV (SEQ ID NO: 12); SVDWWAYGVLLYEMLA (SEQ ID NO: 6); SVDWWAYGVLLYEXLA (SEQ ID NO: 13); EDEDELFQSIME (SEQ ID NO: 7); EDEDELFQSIXE (SEQ ID NO: 14); GERDVRE (SEQ ID NO: 8); GEXDVRE (SEQ ID NO: 15); GERDVXE (SEQ ID NO: 16); GEXDVXE (SEQ ID NO: 17); wherein X is any amino acid except M, P and R. In particular, the peptide may comprise, consist essentially in or consist in at least one of the following sequences: VECTMVEKRVLA (SEQ ID NO: 3); VECTXVEKRVLA (SEQ ID NO: 9); VECTMVEKXVLA (SEQ ID NO: 10); VECTXVEKXVLA (SEQ ID NO: 11); LXYHIQQV (SEQ ID NO: 12); SVDWWAYGVLLYEXLA (SEQ ID NO: 13); EDEDELFQSIXE (SEQ ID NO: 14); GERDVRE (SEQ ID NO: 8); GEXDVRE (SEQ ID NO: 15); GERDVXE (SEQ ID NO: 16); GEXDVXE (SEQ ID NO: 17); wherein X is any amino acid except M, P and R. For instance, the peptide may comprise at least one of the following sequences: VECTMVEKRVLA or VECTTVEKEVLA (SEQ ID NO: 19).

Optionally, the peptide comprises 1, 2, 3, 4, 5, 6, 7, 8, 9, or 10 substitution(s), deletion(s), addition(s), or a mixture thereof, preferably, 1, 2, 3, 4, or 5 substitution(s), deletion(s), addition(s), or a mixture thereof, more preferably, 1, 2, or 3 substitution(s).

Optionally, the peptide may comprise, consist essentially in or consist in at least one of the following sequences: VECTMVEKRVLA (SEQ ID NO: 3) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKRVLA (SEQ ID NO: 9) with optionally modification(s) of an amino acid selected from 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTMVEKXVLA (SEQ ID NO: 10) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; VECTXVEKXVLA (SEQ ID NO: 11) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; LDN; SVDWWAYGVLLYEMLA (SEQ ID NO: 6) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; SVDWWAYGVLLYEXLA (SEQ ID NO: 13) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; EDEDELFQSIME (SEQ ID NO: 7) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; EDEDELFQSIXE (SEQ ID NO: 14) with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; LDN; AFF; PDY; XDY; PEII (SEQ ID NO: 5); XEII (SEQ ID NO: 18); PAK; XAK; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y.

In one aspect, the peptide may comprise, consist essentially in or consist in at least one of the following sequences: VECTMVEKRVLA (SEQ ID NO: 3) with optionally 1, 2, or 3 modification(s) of an amino acid selected from substitution(s) deletion(s), addition(s), and a mixture thereof; VECTXVEKRVLA (SEQ ID NO: 9) with optionally modification(s) of an amino acid selected from 1, 2, or 3 modification(s) of an amino acid selected from substitution(s) deletion(s), addition(s), and a mixture thereof; VECTMVEKXVLA (SEQ ID NO: 10) with optionally 1, 2, or 3 modification(s) of an amino acid selected from substitution(s) deletion(s), addition(s), and a mixture thereof; VECTXVEKXVLA (SEQ ID NO: 11) with optionally 1, 2, or 3 modification(s) of an amino acid selected from substitution(s) deletion(s), addition(s), and a mixture thereof; LMYHIQQV (SEQ ID NO: 4) with optionally 1, 2, or 3 modification(s) of an amino acid selected from substitution(s) deletion(s), addition(s), and a mixture thereof; LXYHIQQV (SEQ ID NO: 12) with optionally 1, 2, or 3 modification(s) of an amino acid selected from substitution(s) deletion(s), addition(s), and a mixture thereof; SVDWWAYGVLLYEMLA (SEQ ID NO: 6) with optionally 1, 2, or 3 modification(s) of an amino acid selected from substitution(s) deletion(s), addition(s), and a mixture thereof; SVDWWAYGVLLYEXLA (SEQ ID NO: 13) with optionally 1, 2, or 3 modification(s) of an amino acid selected from substitution(s) deletion(s), addition(s), and a mixture thereof; EDEDELFQSIME (SEQ ID NO: 7) with optionally 1, 2, or 3 modification(s) of an amino acid selected from substitution(s) deletion(s), addition(s), and a mixture thereof; EDEDELFQSIXE (SEQ ID NO: 14) with optionally 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y.

In particular, the peptide may comprise, consist essentially in or consist in at least one of the following sequences: VECTMVEKRVLA (SEQ ID NO: 3) with optionally 1, 2, or 3 modification(s) of an amino acid selected from substitution(s) deletion(s), addition(s), and a mixture thereof; VECTXVEKRVLA (SEQ ID NO: 9) with optionally modification(s) of an amino acid selected from 1, 2, or 3 modification(s) of an amino acid selected from substitution(s) deletion(s), addition(s), and a mixture thereof; VECTMVEKXVLA (SEQ ID NO: 10) with optionally 1, 2, or 3 modification(s) of an amino acid selected from substitution(s) deletion(s), addition(s), and a mixture thereof; VECTXVEKXVLA (SEQ ID NO: 11) with optionally 1, 2, or 3 modification(s) of an amino acid selected from substitution(s) deletion(s), addition(s), and a mixture thereof; GERDVRE (SEQ ID NO: 8) with optionally 1, 2, or 3 modification(s) of an amino acid selected from substitution(s) deletion(s), addition(s), and a mixture thereof; GEXDVRE (SEQ ID NO: 15) with optionally 1, 2, or 3 modification(s) of an amino acid selected from substitution(s) deletion(s), addition(s), and a mixture thereof; GERDVXE (SEQ ID NO: 16) with optionally 1, 2, or 3 modification(s) of an amino acid selected from substitution(s) deletion(s), addition(s), and a mixture thereof; GEXDVXE (SEQ ID NO: 17) with optionally 1, 2, or 3 modification(s) of an amino acid selected from substitution(s) deletion(s), addition(s), and a mixture thereof; wherein X is any amino acid except M, P and R. Preferably, X an amino acid favorable to an α-helix secondary structure. For instance, X may be selected from the group consisting of A, D, N, C, G, Q, E, H, L, K, F, S, W and Y, more preferably A, D, N, G, Q, E, H, L, K, F, S, W and Y.

For instance, the peptide may comprise at least one of the following sequences:

```
                              (SEQ ID NO: 19)
VECTMVEKRVLA
or

VECTTVEKEVLA.
```

In one aspect, the peptide may comprise, consist essentially in or consist in at least one of the following sequences:

a) VECTXVEKXVLALLDKXXFLTQLHS (SEQ ID NO: 20) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

b) VECTMVEKRVLALLDKXXFLTQLHS (SEQ ID NO: 21) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

c) VECTXVEKRVLALLDKPPFLTQLHS (SEQ ID NO: 22) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

d) VECTMVEKXVLALLDKPPFLTQLHS (SEQ ID NO: 23) wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, with optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof;

and the sequence of any segment of at least 5, 6, 7, 8, 9, 10, 11, 12, 13, 14, 15, 16, 17, 18, 19, 20, 21, 22, 23 or 25 consecutive residues of any sequence a) to d).

In another particular embodiment, the peptide according to the present disclosure is designed or modified in order to maintain it in an alpha helical conformation. As known in the art, this can be achieved via a variety of methods, including modification of the amino acid sequence with substitution of amino acids not critical for biological effects, use of non-natural amino acids, peptide cyclization, and modifications to the peptide backbone or addition of chemical links between amino acids in the peptide chain. Such modifications can be made to peptides, for example, to increase their thermal and protease stability.

In particular, the peptide of the present disclosure is modified by a chemical cross-link. For instance, the peptide can be a stapled peptide. In one embodiment, the peptide of the present disclosure is stapled. The term "stapled peptide" or "stitched peptide", as used herein, refers to an artificially modified peptide in which the peptide secondary structure is stabilized with one or more artificial molecular crosslinks (bridges) that connect adjacent turns of α-helices in the peptide. The methods for preparing stapled peptides are well known in the art, for instance in Verdine & Hilinski (2012, Methods Enzymol, 503, 3-33), WO10033617 and WO10011313, the disclosure of which is incorporated herein by reference.

In one embodiment, the crosslinks of the stapled peptide of the present disclosure are i+3, and/or i+4, and/or i+7 crosslinks. In a peptide, a "i+3 crosslink" is a crosslink between an amino acid, the "i" amino acid, and another amino acid present at a distance of 3 amino acid residues from the i amino acid. In a peptide, a "i+4 crosslink" is a crosslink between an amino acid, the "i" amino acid, and another amino acid present at a distance of 4 amino acid residues from the i amino acid. In a peptide, a "i+7 crosslink" is a crosslink between an amino acid, the "i" amino acid, and another amino acid present at a distance of 7 amino acid residues from the i amino acid.

For the shortest sequences, in particular those including three to four residues, the cross-link is i+3 and i+4 and it is introduced between residues which are outside of this sequence. When the sequences are long enough, the cross-link of i+7 is preferred.

To illustrate this aspect on one particular peptide, the peptide may comprise, consist essentially in or consist in one of the following sequences:

```
                             (SEQ ID NO: 24)
VECTMXEKRVLAX (SEQ ID NO: 25)
VECTXXEKRVLAX (SEQ ID NO: 26)
VECTMXEKXVLAX (SEQ ID NO: 27)
VECTXXEKXVLAX (SEQ ID NO: 28)
VECTXXEKXVLAXLDKXXFLTQLHS (SEQ ID NO: 29)
VECTMXEKRVLAXLDKXXFLTQLHS (SEQ ID NO: 30)
VECTXXEKRVLAXLDKPPFLTQLHS (SEQ ID NO: 31)
VECTMXEKXVLAXLDKPPFLTQLHS
``` wherein the residues which are bold and underlined X carry the stapling and is any amino acid derivative suitable for stapling; and wherein X is any amino acid except M, P and R, preferably, an amino acid favorable to an α-helix secondary structure, more preferably selected from the group consisting of A, D, N, C, G, Q, E, H, L, K, F, S, W and Y, still more preferably A, D, N, G, Q, E, H, L, K, F, S, W and Y, and with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

For instance, in the context of a i+7 stapling, the first X is a 2-(7-octenyl)amino acid (for instance a 2-(7-octenyl) alanine or a 2-(7-octenyl)arginine) and the second X is a 2-(4-pentenyl)amino acid (for instance a 2-(4-pentenyl)alanine or a 2-(4-pentenyl)serine). Specific combinations can be 2-(7-octenyl)alanine and 2-(4-pentenyl)alanine; 2-(7-octenyl)alanine and 2-(4-pentenyl)serine; 2-(7-octenyl)arginine and 2-(4-pentenyl)alanine; or 2-(7-octenyl)arginine and 2-(4-pentenyl)serine.

In a particular embodiment, the peptide can be

```
                              (SEQ ID NO: 32)
VECTTREKEVLASLDKAAFLTQLHS
``` wherein R and S carry the stapling, being preferably 2-(7-octenyl)arginine and 2-(4-pentenyl)serine, respectively;

with the sequence having optionally 1, 2, 3, 4, or 5 modification(s) of an amino acid selected from substitution(s), deletion(s), addition(s), and a mixture thereof, more preferably, 1, 2, or 3 modification(s) of an amino acid selected from substitution(s) deletion(s), addition(s), and a mixture thereof.

In a particular embodiment, the peptide according to the present disclosure is a cyclic peptide. As used herein, the term "cyclic peptide" or "circular peptide" are equivalent and refers to a peptide in which the N-terminus and the C-terminus, or the N-terminus and the side chain of another amino acid, preferably the C-terminal amino acid, or the C-terminus and the side chain of another amino acid, preferably the N-terminal amino acid, or the side chain of an amino acid and the side chain of another amino acid, preferably the N-terminal amino acid and the C-terminal amino acid, are linked with a covalent bond that generates a ring structure. As used herein, the term "N-terminus", "amino-terminus", "NH2-terminus", "N-terminal end" and "amine-terminus" are equivalent and refer to the free amine group (—NH2) present on the first amino acid of the peptide. As used herein, the term "C-terminus", "carboxyl-terminus", "carboxy-terminus", "C-terminal end", and "COOH-terminus" are equivalent and refer to the free carboxyl group (—COOH) present on the last amino acid of the peptide.

In one embodiment, the peptide according to the present disclosure has a length of less than 80 amino acids, more preferably less than 60 amino acids, still preferably less than 40 amino acids, and even more preferably less than 30 amino acids. In a particular embodiment, the peptide according to the present disclosure has a length of less than 25 amino acids. In another particular embodiment, the peptide according to the present disclosure has a length of less than 20 amino acids, preferably of less than 15 amino acids. Preferably, the peptide has a minimum length greater than 4, 5, 6, 7, 8, 9, 10, 11, 12, 13, 14, 15, 16, 17, 18, 19, or 20 amino acids. For instance, the peptide has a length of at least 4 amino acids and less than 40 amino acids, preferably a length of at least 4 amino acids and less than 30 amino acids; more preferably of at least 6 amino acids and less than 25 amino acids.

In one embodiment, the peptide according to the present disclosure is capable of interfering with ALMS1-PKC interaction, in particular to decrease or prevent the interaction between ALMS1 and αPKC. In other words, the peptide according to the present disclosure is capable of blocking the interaction between ALMS1 and αPKC. Alternatively, the peptide according to the present disclosure is not capable of interfering with ALMS1-PKC interaction, in particular to decrease or prevent the interaction between ALMS1 and αPKC. In other words, the peptide according to the present disclosure is not capable of blocking the interaction between ALMS1 and αPKC.

In order to determine the effect of a peptide on the binding of αPKC to ALMS1, any technology known by the person skilled in the art can be carried out, in particular any method suitable for determining protein interactions. For example, recombinant or purified native ALMS1 or αPKC can be bound to a surface plasmon resonance ship and the other molecule flowed over the chip to assess the binding affinity, for example in a Biacore (General Electric, USA) machine.

The effect of peptide(s) on the binding of αPKC to ALMS1 is determining by measuring the binding of αPKC to ALMS1 in absence and in presence of the tested peptide(s) and by comparing the bindings of αPKC to ALMS1.

In particular, immunoprecipitation assay using ALMS1 as bait can be carried. The assay can be carried out with cells, in particular adipocytes, cultured in absence and/or presence of insulin, preferably in absence of insulin. The peptides to be tested are added in the culture medium. Then, αPKC is immunodetected.

By "decreased", "decrease" or "prevent" is intended to refer to a binding decreased by at least 10, 20, 30, 40, 50, 60, 70, 80 or 90% when compared to the binding measured in absence of the tested molecule in the same conditions.

In one embodiment, the peptide according to the present disclosure is capable of decreasing the expression of FATP2 in adipose tissue.

FATP2 is also called Solute Carrier Family 27 Member 2 (SLC27A2). This protein is disclosed in the database UniProtKB under 014975. The gene is described in UniGene database under Hs.11729. Sequences of reference can be found in NCBI under NP 003636.2 and NM_003645.3 for the isoform 1 and under NP_001153101.1 and NM_001159629.1. for the isoform 2.

By "decreased" or "decrease" is intended to refer to an expression decreased by at least 10, 20, 30, 40, 50, 60, 70, 80 or 90% when compared to the expression measured in absence of the peptide in the same conditions. The expression can be measured either at the protein level (e.g., with antibodies) or at the mRNA level.

The expression can be measured at the protein level by any available method such as immuno-histochemistry, semi-quantitative Western-blot or by protein or antibody arrays. Antibodies directed to FATP2 are commercially available, for instance from Origene, ref TA350424 or TA333990; or Santa Cruz Biotechnology, ref sc-393906.

The expression can also be measured at the mRNA level by any available method. Preferably, the expression level of FATP2 is determined by measuring the quantity of the mRNA transcripts by quantitative RT-PCR, real time quantitative RT-PCR, Nanostring technology PCR or by high-throughput sequencing technology such as RNA-Seq or sequencing technologies using microfluidic systems. More specifically, the expression is measured by the method specified in the Example section.

In a particular embodiment, the effect on the FATP2 expression caused by the peptide in the adipose tissue is preferably specific to FATP2. In this embodiment, the peptide can have no or less effect on the expression of the other FATPs, i.e. FATP1, FATP3, FATP4, FATP5 and FATP6, in the adipose tissue, in particular of a mammal.

In one embodiment, the peptide according to the present disclosure is capable of decreases the liver steatosis, the amount of fat in liver, the size of fat droplets in liver, and/or the fatty liver index.

In a particular embodiment, the peptide according to the present disclosure presents the following features
- it does not simultaneously comprise one methionine, one proline and one arginine;
- it adopts a secondary structure which is a helix, preferably an alpha helix; and
- it comprises, consists essentially in or consists in a sequence from a segment of the kinase domain of a PKC (Protein Kinase C);

and further present one, two, three, four or all following features:
- it modifies the expression levels of the FATPs expression in adipose tissue, preferentially it decreases the FATP2 expression in adipose tissue;
- it decreases the liver steatosis, the amount of fat in liver, the size of fat droplets in liver, and/or the fatty liver index;
- it has a length of at least 4 amino acids and less than 40 amino acids, preferably a length of at least 4 amino acids and less than 30 amino acids, more preferably of at least 4 amino acids and less than 25 amino acids;
- it adopts a secondary structure which is a helix, preferably an alpha helix;
- it is modified by a cross-link.

In a more specific embodiment, the peptide according to the present disclosure presents the following features:
- it decreases the liver steatosis, the amount of fat in liver, the size of fat droplets in liver, and/or the fatty liver index;
- it does not simultaneously comprise one methionine, one proline and one arginine;
- it has a length of at least 4 amino acids and less than 40 amino acids, preferably a length of at least 4 amino acids and less than 30 amino acids, more preferably of at least 4 amino acids and less than 25 amino acids;
- it adopts a secondary structure which is a helix, preferably an alpha helix.

In another more specific embodiment, the peptide according to the present disclosure presents the following features:
- it decreases the FATP2 expression in adipose tissue;
- it does not simultaneously comprise one methionine, one proline and one arginine;
- it has a length of at least 4 amino acids and less than 40 amino acids, preferably a length of at least 4 amino acids and less than 30 amino acids, more preferably of at least 4 amino acids and less than 25 amino acids;
- it adopts a secondary structure which is a helix, preferably an alpha helix.

In one embodiment, the peptide according to the present disclosure is capable of decreasing the expression of collagen, in particular collagen IV, and LOXL2. Preferentially it decreases the expression of LOXL2, in particular the LOXL2 expression in liver and/or plasma.

It can be capable of decreasing the lysophosphatidylcholine (LPC) lipid content in the tissues and in circulation, preferentially the 18:2 LPC.

The peptide according to the present disclosure may further comprise a moiety facilitating its cellular uptake or entry, in particular a PTD (protein transduction domain). PTD generally comprises a certain amino acid sequence of 10 to 20 amino acids (Matsushita and Matsui, (2005), J Mol Med 83, 324-328; Vivès et al, Biochimic et Biophysica Acta, 2008, 1786, 126-138). PTD is mainly composed of basic amino acids such as arginine or lysine, and representative examples of the PTD include arginine rich peptides such as poly $R_8$ (RRRRRRRR (SEQ ID NO: 33)) or (RRPRRPRR-PRRPRRP (SEQ ID NO: 34)), antennapedia or penetratin peptide such as (RQIKIWFQNRRMKWKK (SEQ ID NO: 35)) or HIV-Tat (YGRKKRRQRRR (SEQ ID NO: 36)).

The peptide according to the present disclosure can be made of natural amino acids and/or unnatural amino acids. The term "unnatural amino acids" is defined as an analog or derivative of a natural amino acid (i.e., Alanine, Valine, Glycine, Leucine, Isoleucine, Lysine, Arginine, Glutamic acid, Glutamine, Aspartic acid, Asparagine, Histidine, Tyrosine, Phenylalanine, Tryptophan, Serine, Proline, Threonine, Cysteine, Methionine). They present a modified side chain, e.g. shorter, longer or with different functional groups. Isomers D and L are contemplated, in particular because isomers D are not sensible to proteases. In addition, modifications in some or all peptide bounds are also contemplated in order to increase the proteolysis resistance, in particular by (—CO—NH—) by (—CH$_2$—NH—), (—NH—CO—), (—CH$_2$—O—), (—CH$_2$—S—), (—CH$_2$—CH$_2$—), (—CO—CH$_2$—), (—CHOH—CH$_2$—), (—N═N—), and/or (—CH═CH—). The peptide can present a carboxylic C terminal end (—COO$^-$) and an amide one (—CONH$_2$). The peptide can also be D-retro-inverso sequence of a peptide as disclosed herein. The N terminal can be modified, especially with an acetyl radical.

Optionally, the peptide can be PEGylated in order to increase its stability. Further optionally the peptide can be formulated in non-aqueous protic solvent solutions such as propylene glycol and polyethylene glycol. The peptide may also be packaged into poly lactic co-glycolic acid microsphere depot formulation. Many sustained-release delivery systems exist, and many of these are appropriate for use in the present disclosure. For example, polymer-based slow-release compositions based upon degradable polymers such as PLGA, poly-lactate or poly-glycolate are suitable, as are lipid-based depot compositions, such as those described in WO2005/117830 and/or WO2006/075124, the complete disclosures of which are being hereby incorporated by reference. The formulation of active agents into biodegradable polymer depot formulations is well established and well known in the art, and the peptides of the present disclosure may thus be formulated with these using known methods. Preferably, the composition of the present disclosure is capable of releasing the peptide at a functional concentration for at least 1 month.

In an additional aspect, the peptide according to the present disclosure decreases the phenomenon of steatosis and any hepatic disorder associated with NAFLD or NASH in the liver. The phenomenon of steatosis in the liver can be assessed by any method known from the man skilled in the art. In particular, it is assessed by the method described in the example section. For instance, the steatosis can be measured by imaging or biopsy. Peptides that decrease the phenomenon of steatosis in the liver can be conveniently screened for using any technology known in the art. In particular, a method for assessing the steatosis in the liver can comprise any method suitable for measuring the fat in the liver, the size of the lipid droplets in the liver and/or measuring the fatty liver index (Bedgni et al, BMC Gastroenterol. 2006 Nov. 2; 6:33).

By "a peptide" is intended to refer to a peptide as disclosed above or a combination of different peptides as disclosed above. For instance, 2, 3, 4, 5 or 6 different peptides can be used, preferably 2 or 3, more preferably 2.

Combinations

The peptide(s) according to the present disclosure can be used in combination with one or more additional active drugs, for instance an anti-diabetic drug, a hypolipidemic agent, an anti-obesity agent, an anti-hypertensive agent, an anti-steatotic drug, an anti-inflammatory agent, and an agonist of peroxisome proliferator-activator receptors.

Accordingly, the present invention relates to:
a peptide or a pharmaceutical composition comprising a peptide as disclosed herein for use in the treatment or prevention of a disease, in combination with one or more additional active drugs, in particular as disclosed herein; wherein the disease is selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

a pharmaceutical composition comprising a peptide as disclosed herein and one or more additional active drugs, in particular as disclosed herein, for use in the treatment or prevention of a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

a product, combined preparation or kit comprising a peptide according to the present disclosure and one or more additional active drugs, in particular as disclosed herein, for simultaneous, separate or sequential use in the treatment or prevention of a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

the use of a peptide for the manufacture of a medicine for the treatment or prevention of a disease in combination with one or more additional active drugs, in particular as disclosed herein, wherein the disease is selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

the use of a peptide as disclosed herein and one or more additional active drugs, in particular as disclosed herein, for the manufacture of a medicine for the treatment or prevention of a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

a method for the treatment or prevention of a disease in a subject, comprising administering a therapeutically effective amount of a peptide as disclosed herein and a therapeutically effective amount of one or more additional active drugs, in particular as disclosed herein, wherein the disease is selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis;

a method for the treatment or prevention of a disease in a subject, comprising administering a therapeutically effective amount of a pharmaceutical composition comprising a peptide as disclosed herein and one or more additional active drugs, in particular as disclosed herein, wherein the disease is selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis, especially a fibrosis selected from the group consisting of a liver fibrosis including cirrhosis, a renal fibrosis, a cardiac fibrosis including an atrial fibrosis, an endomyocardial fibrosis and old myocardial infarction, a pulmonary fibrosis including cystic fibrosis and radio-induced lung fibrosis, a vascular fibrosis such as an arterial fibrosis, a brain fibrosis, a myelofibrosis, an arthrofibrosis, an intestinal fibrosis, a peritoneal fibrosis, a retroperitoneal fibrosis and a skin fibrosis.

In particular, a therapeutic or sub-therapeutic effective amount of one or more additional active drugs can be used. By "sub-therapeutic" is intended to refer to an amount that can be for instance 90, 80, 70, 60, 50, 40, 30, 20 or 10% of the conventional therapeutic dosage (in particular for the same indication and/or the same administration route and/or frequency of administration).

The anti-diabetic drug can be for instance insulin, insulin derivatives and mimetics; insulin secretagogues such as the sulfonylureas (e.g., chlorpropamide, tolazamide, acetohexamide, tolbutamide, glyburide, glimepiride, glipizide); gliflozins such as emplagliflozin and dapagliflozin; glyburide and Amaryl; liraglutide (NN2211); insulinotropic sulfonylurea receptor ligands such as meglitinides, e.g. nateglinide and repaglinide; thiazolidinediones (e.g., rosiglitazone (AVANDIA), troglitazone (REZULIN), pioglitazone (ACTOS), balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; protein tyrosine phosphatase-IB (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095 or canagliflozin; glycogen phosphorylase A inhibitors such as BAY R3401; biguanides such as metformin and other agents that act by promoting glucose utilization, reducing hepatic glucose production and/or diminishing intestinal glucose output; alpha-glucosidase inhibitors such as acarbose and migiitoi) and other agents that slow down carbohydrate digestion and consequently absorption from the gut and reduce postprandial hyperglycemia; GLP-1 (glucagon like peptide-1), GLP-1 analogs such as Exendin-4 and GLP-1 mimetics; and DPPIV (dipeptidyl peptidase IV) inhibitors such as vildagliptin. It can also be an anti-diabetic drug described in Expert Opin Investig Drugs 2003, 12(4): 623-633, FIGS. 1 to 7. Antidiabetic drug may also include a molecule preventing the binding of αPKC and ALMS1 such as those disclosed in WO 2015/114062, the disclosure thereof being incorporated herein by reference.

The hypolipidemic agent can be for instance 3-hydroxy-3-methyl-glutaryl coenzyme A (HMG-CoA) reductase inhibitors, e.g. lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands such as obeticholic acid; bile acid sequenstrants, such as cholestyramine and colesevelam; fibrates; nicotinic acid and aspirin; aramchol, a transmembrane G protein-coupled receptor (TGR) 5 agonist.

The anti-obesity agent can be for instance orlistat, rimonabant, phentermine, topiramate, qnexa, and locaserin.

The anti-hypertensive agent can be for instance loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors such as sacubitril; ACE/NEP inhibitors such as omapatrilat, sampatrilat and fasidotril; angiotensin II antagonists such as candesartan, eprosartan, irbesartan, losartan, telmisartan and valsartan, in particular valsartan; combinantions of NEP inhibitors and angiotensin II antagonists such as sacubitril and valsartan (i.e. Entresto); renin inhibitors such as ditekiren, zankiren, terlakiren, aliskiren, RO 66-1132 and RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

The agonist of peroxisome proliferator-activator receptors can be for instance fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzene-sulfonyl}-2,3-dihydro-1H-indole-2-carboxylic or a salt thereof.

Other drugs of interest can be for instance cenicriviroc, simtuzumab, selonsertib, emricasan. In a particular embodiment, the one or more additional active drugs used in combination with the peptide can be selected among: a GLP-1 analog such as liraglutide, obeticholic acid, a gliflozin, simtuzumab (GS 6624), cenicriviroc, aramchol, a Galectin 3 inhibitor such as GR-MD-02, a TGR5 agonist and a dual FXR/TGR5 agonist such as INT-777 or INT-767, and emricasan.

The anti-inflammatory agent can be any drug known by the skilled person such as nonsteroidal anti-inflammatory agents (NSAIDs), including salicylic acid, ibuprofen in its various forms and naproxen in its various forms, a steroidal anti-inflammatory such as corticosteroids, an anti-inflammatory anti-TNF alpha antibody and combinations thereof.

The form of the pharmaceutical compositions, the route of administration, the dosage and the regimen naturally depend upon the condition to be treated, the severity of the illness, the age, weight, and sex of the patient, etc.

The pharmaceutical or therapeutic compositions of the present disclosure can be formulated for a topical, oral, parenteral, intranasal, intravenous, intramuscular, subcutaneous or intraocular administration and the like.

The peptide used in the pharmaceutical composition of the present disclosure is present in a therapeutically effective amount.

The pharmaceutical composition comprising the peptide is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

In one aspect, the present invention provides a stable formulation for parenteral injection of the pharmaceutical composition according to the present disclosure comprising a peptide or a salt thereof, wherein the peptide has been dried and then is reconstituted in a solvent prior to use. The peptide (or, in embodiments where the formulation comprises two or more peptides, each of the peptides) is mixed with a non-volatile buffer and dried to a dry peptide powder. Suitable buffers include, but are not limited to, glycine buffers, citrate buffers, phosphate buffers, and mixtures thereof. In one embodiment, the buffer is a glycine buffer. In another embodiment, the buffer is a mixture of citrate buffer and phosphate buffer. In some embodiments, wherein the formulation comprises two or more peptides, the first and second buffer are the same. In some embodiments, wherein the formulation comprises two or more peptides, the first and the second buffer are different. Alternatively, the pharmaceutical composition according to the present disclosure may be stored in an aqueous state. The solution may contain, if desired, further additives or excipients, which must be compatible with the active principle and, if they are not removed during the freeze-drying stage, they must also be compatible with the route of administration. For parenteral administration, the composition may be injected intradermally, subcutaneously, intramuscularly, or intravenously. Preferably, the composition or peptide is injected or to be injected subcutaneously, in particular in the fat tissue.

It may preferably be placed with a mini-osmotic pump or other controlled delivery device implanted into the body. Preferably, it may be mixed with other compounds to make a depot slow release formulation. A preferred route of administration is subcutaneous injection, for instance by using a disposable or multiunit dispensing device, similar to an insulin pen. The peptide can also be administered by a device allowing the subcutaneous administration without any needle, a non-invasive system.

In addition, the peptide can be administered by using any drug delivery system available. In particular, the use of recombinant human hyaluronidase enzyme, rHuPH20, to enable and optimize subcutaneous drug delivery for appropriate co-administered therapies is contemplated.

With the technology, some biologics and compounds that are administered intravenously may instead be delivered subcutaneously, or under the skin, potentially providing a better experience for patients, and increasing health system efficiency by reducing administration time, injection pain and infusion site reactions.

In one embodiment, the peptide of the present disclosure may be mixed with other compounds to make a depot slow release formulation. This may then be injected subcutaneously to form a slow release depot.

For oral administration, the composition can be formulated into conventional oral dosage forms such as tablets, capsules, powders, granules and liquid preparations such as syrups, elixirs, and concentrated drops. Non-toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, intrapulmonary inhalation, rectal or vaginal suppositories can be used. In one embodiment, the invention may be administered by the intrapulmonary route using either a dry powder or liquid formulation administered using an intrapulmonary drug delivery device according to methods known in the art. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the present disclosure may be formulated to release the active drug substantially immediately upon administration or at any predetermined time or time period after administration.

Pharmaceutical compositions according to the present disclosure can comprise one or more peptides of the present disclosure associated with pharmaceutically acceptable excipients and/or carriers. These excipients and/or carriers are chosen according to the form of administration as described above.

In a particular embodiment, the pharmaceutical composition according to the present disclosure comprises between 0.01 ng and 10 g of the peptide of the present disclosure. In one embodiment, pharmaceutical composition according to the present disclosure comprises between 0.1 ng and 1 g of the peptide of the present disclosure.

All the references cited in this application, including scientific articles and summaries, published patent applications, granted patents or any other reference, are entirely incorporated herein by reference, which includes all the results, tables, figures and texts of theses references.

Although having different meanings, the terms "comprising", "having", "consisting in" and "containing" can be replaced one for the other in the entire application.

Further aspects and advantages of the present disclosure will be described in the following examples, which should be regarded as illustrative and not limiting.

EXAMPLES

Example 1: Effect of Adipose Tissue Targeted PATAD Treatment on Expression Levels of Key Fatty Acids Transporters and Receptors 11 Days Post Injection As PATAD subcutaneous injection relates to restoration of glucose absorption in the adipose tissue, the inventors measured the expression levels of all 6 isoforms for the FATPs (1-6) (Fatty acid transport protein 1-6) and the 4 isoforms of the FFAR (Free Fatty Acid Receptor) to assess any effect on these genes.

Interestingly, PATAD injections induced a very specific and drastic decrease in FAPT2 in the adipose tissue allowing to correlate the effect of PATAD treatment directly on the FATP2 expression drop (FIG. 1A). Since it was previously shown that PATAD peptide does not circulate in the body, that its effect was limited to the adipose tissue and also based on its mechanism of action which is to interfere with ALMS1-PKC interaction, PATAD's novel action in the adipose tissue is to decrease FATP2. The expression levels of the transporters and receptors in the two other major organs can be related to indirect effect (FIG. 1B-C).

Example 2: ADPIF Peptide is More Active than PATAD Peptide in Decreasing FATP2 Expression Levels in the Adipose Tissue Mice were injected with a single dose of either scramble peptide or PATAD or ADPIF. 11 days post injection, the mice were euthanized and adipose tissue was sampled for RNA extraction followed by real-time PCR. The expression level of FATP2 is similar to the lean control whereas PATAD, although effective in reducing FATP2 expression levels in the adipose tissue, is less effective than ADPIF (FIG. 2A).

Example 3: ADPIF is Effective in Increasing Circulating Levels of GLP-1 11 Days Post Adipose Tissue Injection Mice were injected with a single dose of either scramble peptide or PATAD or ADPIF. 11 days post injection, the mice were euthanized, and plasma was obtained and used for determination of circulating GLP1 from mice with the indicated treatment. Both PATAD and ADPIF restored high circulating levels of GLP1, with ADPIF inducing a greater increase than PATAD (FIG. 2B).

Example 4: Protective Effect on Liver after 3 Months of a Single Injection of Adipose Tissue Targeted Either PATAD or ADPIF Treatment Mice presented were euthanized and their plasma and organs were sampled for analysis. The ratio of liver weight to body weight versus age was determined and presented in FIG. 3B. The size of the liver in response to the PATAD treatment was clearly decreased compared to controls that were DIO diabetic male controls that received only the vehicle. Cryosection of the livers were then stained with Adipored and DAPI to detect the level of lipid droplets. Mice treated with PATAD or ADPIF clearly showed a decrease in the size of the hepatic lipid droplets (FIG. 3A, right panel; FIG. 7, right panel). Hepatic function is assessed by two liver related strong biomarkers namely (AST (Aspartate Aminotransferase) and ALT (Alanine Aminotransferase)), whose levels increase proportionately with liver damage. Interestingly, mice treated with PATAD or ADPIF (after a 3-month period with a single subcutaneous peptide injection) exhibit a dramatic decrease in these two robust hepatic biomarkers (FIG. 3C) indicating a protective effect of PATAD and ADPIF on the liver related to a decrease in the phenomenon of steatosis. PATAD and ADPIF are both effective in reducing circulating levels of AST and ALT. ADPIF is more active in reducing circulating levels of ALT, which translates improvement of liver cell injury.

Example 5: ADPIF Peptide is More Active than PATAD Peptide in Preventing Hyperglycemia These are results obtained from series of glucose tolerance test (GTT) and data from two-time points namely 30 minutes and 120 minutes were used to generate these curves for both control and PATAD treated diet induced obese (DIO) and diabetic wild type male C57/B6 mice (control).

These data show that the peptide-based ADPIF have a better effect in glucose tolerance test than the PATAD peptide (FIG. 4).

Example 6. ADPIF Peptide is More Active than PATAD Peptides in Reducing Hepatic Levels of LOXL2 and FABP4 Proteins LOXL2 is the enzyme promoting the development of fibrotic lesions by favoring the polymerization of collagen and FABP4 is a protein involved in lipid metabolism whose level increases with increasing lipid deposition in the liver. 3 months post treatment with a unique injection, liver extracts from the mice with the indicated mice were used and these data show that peptide ADPIF is more potent than PATAD in decreasing the hepatic levels of LOXL2, thereby decreasing the ability to generate more fibrotic lesions in the liver and in decreasing the levels of FABP4, which correlates with a decrease in liver triglycerides levels (FIG. 5).

Example 7: Circulating Lipid Profile in Response to ADPIF Treatment in the Adipose Tissue ADPIF adipose tissue injection has proven to be unexpectedly liver protective relative to a specific decrease in expression levels of FATP2 in the adipose tissue and an associated profile of the FATPs and FFARs in the muscles and liver. As these changes impact circulating population of the different lipids. Ceramides are a group of biological active lipids known to be involved in NAFLD. We measured and determined the effect of ADPIF injections on the ceramides profile following 3 injections of ADPIF at a frequency of one injection per week in the subcutaneous adipose tissue. ADPIF globally induces a decrease in the hepatic ceramides content with variations between the different ceramides (FIG. 6).

Example 8: ADPIF is Effective in Decreasing the Size of the Lipid Droplets in the Liver In FIG. 7, cryosections from livers of treated mice (with same dosage regiment as in example 6) were stained for lipid droplets which evidenced a global decrease in the sizes of the lipid droplets in the liver post ADPIF treatment thereby indicating a decrease in the accumulation of lipids in the liver.

Example 9: ADPIF Treatment in the Adipose Tissue Surprisingly Repressed the Expression Levels of Key Lipogenesis and Modulating Enzymes in the Liver ACC and FASN form part of the lipogenesis pathway by which fatty acids are synthesized in the liver, together with the Srebf1 which is a key protein involved in lipid handling. Following ADPIF treatment, these enzymes were repressed indicating that ADPIF action following its administration in the adipose tissue is able to block de novo lipogenesis in the liver (FIG. 8).

Figure 9A:
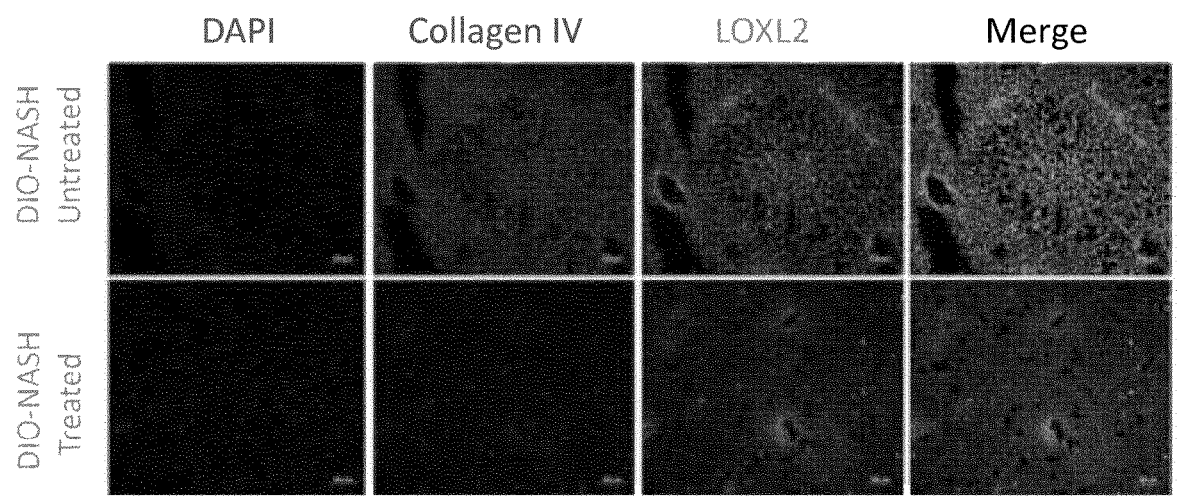
Figure 9B:
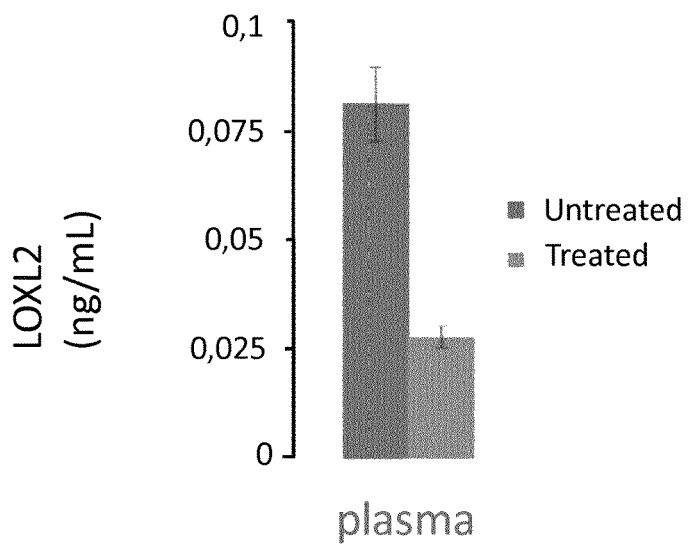
Figure 9C:
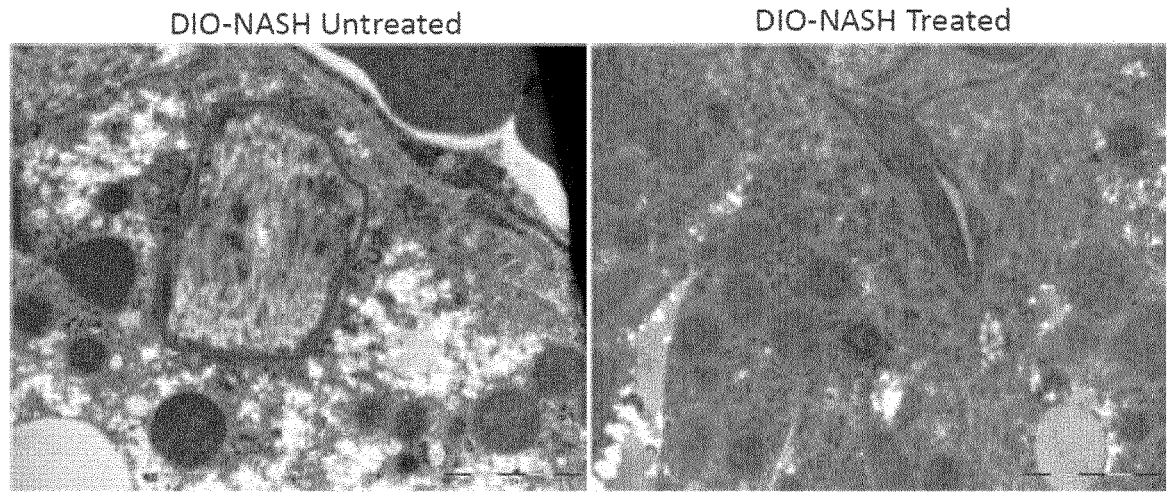

Examples 10: ADPIF Treatment in the Adipose Tissue Blocks the Progression of Hepatic Fibrosis in DIO-NASH Mouse Model Liver cryosections from ADPIF treated mice (same as in example 8) were used for immunodetection of either LOXL2 or Collagen IV and showed that ADPIF was effective in preventing the progression of fibrotic markers (FIG. 9A). The levels of secreted LOXL2 in the plasma was also significantly reduced (FIG. 9B). As a results of the decrease in LOXL2 and the decrease of collagen depots, fibrotic lesions readily detected in the untreated DIO-NASH liver (FIG. 9C, left panel) on transmitted electron microscopy were no longer detected in ADPIF treated livers.

Example 11. ADPIF Selectively Reduces Targeted Lysophosphatidylcholines (LPC) in the Liver and Other Tissues Lipid contents for LPCs were analyzed 3 months post ADPIF injection in the adipose tissue to see how ADPIF could impact the levels of LPCs, known substrate for autotaxin, a key secreted enzyme playing a role in fibrosis progression. Surprisingly, ADPIF was effective in reducing selective LPCS, in the tested organs with LPC18:2 presenting the most prominent reduction in the pancreas, adipose tissue and liver (FIG. 10).

Example 12. ADPIF Peptide is Effective in Preventing Collagen IV Depots in the Kidney Hence Protecting the Kidney from Fibrosis Cryosections of kidneys from DIO vehicle treated and DIO ADPIF treated mice 3 months post treatment, were immunostained for collage IV deposition and tight junction with a ZO-1 antibody to assess the effect of ADPIF peptide on fibrosis progression in other soft tissues. Surprisingly, a clear reduction of Collagen IV was observed in the kidneys of the ADPIF-treated mice compared to the vehicle treated mice indicating that ADPIF peptide was also effective in protecting the kidney from fibrosis (FIG. 11).

Materials & Methods

Mice Husbandry

For this study, mice were on a C57/BL6 genetic background. All animals were housed in a temperature and humidity controlled facility, with a 12 h-light/12 h-dark cycle fed during the whole phase mice will be fed with a 60% high fat diet from Research Diets (D12492), and tap water will be provided ad libitum. Mice were fed and tested regularly for glucose tolerance test for their glucose tolerance and once they were glucose intolerant they were used for treatment.

Peptide Sequences and Synthesis

PATAD is the name given to a series of peptides derived from the PKC alpha isoform that are biologically active with the ability to trigger glucose absorption specifically in the adipose tissue.

Stapled peptide sequence A: VE CTM-[2-(4-pentenyl) alanine]-EK RVL A-[2-(4-pentenyl) alanine]-L DKP PFL TQL HS (SEQ ID NO: 49)

Stapled peptide sequence B: S-[2-(4-pentenyl) alanine]-CKG LMT-[2-(4-pentenyl) alanine]-HP AKR LGC GPE G (SEQ ID NO: 50)

Scrambled peptide sequence A: KEVPVDTCHLTLMLL-FRSVALKQHPE (SEQ ID NO: 51) Scrambled peptide sequence B: SAECKGRHGTPPGKLMICKGL (SEQ ID NO: 22)

ADPIF is the name given to a series of peptides derived from the PKC alpha isoform derivate to PATAD peptide and which present two specific mutations.

Stapled peptide ADPIF sequence: VECTTREKEV-LASLDKAAFLTQLHS (SEQ ID NO: 32)

wherein R and S carry the stapling, being preferably 2-(7-octenyl)arginine and 2-(4-pentenyl)serine, respectively.

The stapled and scrambled peptides were purchased from CPC, USA with a 95% purity.

All peptides were initially dissolved in DMSO and then diluted in sterile saline solution at a concentration of 10 ng/µL. 2.5 µL of each peptide (stapled or scrambled) were mixed and then injected directly in the subcutaneaous adipose tissue in each mouse.

Dosage Regimen of the Peptides

Control mice were injected either with the Scramble controls or with vehicle (0.9% saline solution) (retroperitoneal fat/subcutaneous injection: one injection at DO and the indicated tests performed. Treated mice were injected with the mixture of two PATAD stapled peptides and with ADPIF stapled peptide following the same procedure with the PATAD peptides and with ADPIF peptide test item (retroperitoneal fat/subcutaneous injection: one injection at D0 and the indicated tests performed). In a second series of experiment, ADPIF was injected once per week at a dosage of 25 ug per mouse in the subcutaneous adipose tissue in the retroperitoneal area for 3 weeks and the mice were euthanized one week after the last injection. Mice were euthanized ad tissue samples and plasma were isolated and kept at −80° C. for further testings.

RNA Extraction, cDNA Synthesis, q-PCR and Taqman

Total RNA was prepared from the different tissues and cells using a RiboPure™ kit (Catalog #: AM1924; Ambion) followed by a DNAse treatment with the TURBO DNA-free™ (Catalog #: AM 1907; Ambion). RNA integrity was assessed by gel electrophoresis and RNA concentration by Eppendorf Biophotometer Plus with the Hellma® Tray Cell (Catalog #: 105.810-uvs; Hellma). Reverse transcription of 1 µg total RNA to cDNA was performed using the BioRadiScript™ cDNA synthesis kit (Catalog #: 170-8891; Bio-Rad). Real-time quantitative polymerase chain reaction amplification was performed in a BioRad CFX96 TM Real-Time System using the iQ™ SYBR® Green Supermix (Catalog #: 170-8886; BioRAd) and primer sets optimized for tested targets for SYBR Green-based real-time PCR for the real-time PCR. Taqman analysis was carried out with the specific gene assay with the Taqman® Fast Advanced Master Mix (Catalog #: 4444557; Applied Biosystems). The normalized fold expression of the target gene was calculated using the comparative cycle threshold ($C_t$) method by normalizing target mRNA $C_t$ to those for GAPDH using the CFX Manager Software Version 1.5 and was verified using the Lin-Reg program (Ruijter et al., 2009). All primer pairs were purchased from either Biorad or from Quantitect.

Primer specifications are found in the table below:

| Gene name | Primer name | Sequences | SEQ ID NO: | Fragment size |
|---|---|---|---|---|
| Fatp1 | Mu_Slc27a1-RT-ex3F | TGCTTTGGTT TCTGGGACTT | 37 | 156 bp |
| | Mu_Slc27a1-RT-ex4R | GCTCTAGCCG AACACGAATC | 38 | |
| Fatp2 | Mu_Slc27a2-RT-ex4F | TGGACAAAGT AGACGGAGTG TC | 39 | 165 bp |
| | Mu_Slc27a2-RT-ex5R | TAGCAAGGCC TGTCCCATAC | 40 | |
| Fatp3 | Mu_Slc27a3-RT-ex9F | TGAGAACTTG CCACCGTATG | 41 | 171 bp |
| | Mu_Slc27a3-RT-Ex10R | GGCAGGTAGG CCCCTATATC | 42 | |
| Fatp4 | Mu_Slc27a4-RT-ex2F | GTTTCATCCG GGTCTTCATC | 43 | 184 bp |
| | Mu_Slc27a4-RT-ex3R | GTGTCTGTGC CCTCGAAAAT | 44 | |
| Fatp5 | Mu_Slc27a5-RT-ex4F | AAGTTCTCTG CCTCCCGATT | 45 | 191 bp |
| | Mu_Slc27a5-RT-ex5R | CAAAGCGTTG CTGGAAGTTT | 46 | |
| Fatp6 | Mu_Slc27a6-RT-ex1F | TCGATTCCCT CCTACACTGC | 47 | 204 bp |
| | Mu_Slc27a6-RT-ex2R | TTGGTGGTAC TGGCTCATCA | 48 | |

Primers from Quantitect were: Srebf1: QT00167055, Acc: QT01554441 and for Fasn: QT00149240.

AdipoRed Staining of Liver Sections

Livers were isolated and briefly washed in PBS buffer (pH 7.4). after weighing the dried liver, for the liver to body weight ratio, a sliced sample of the liver were then placed in 4% paraformaldehyde (in 0.1M sodium phosphate buffer, pH 7.2) for 15 min, washed in PBS and incubated in AdipoRed dye (1/25; Lonza, Switzerland) with 30 µM DAPI (Sigma-Aldrich, USA) for 15 minutes. After 3 washes with PBS samples were mounted on slides and pictures were taken using Zeiss microscope.

Immunofluorescence Experiments

For immunofluorescence experiments, liver and kidneys freshly sampled were included in Optimal Cutting Temperature Compound™ (OCT™, Catalog #4583, Tissue-Tek® OCT™, Sakura® Finetek, Torrance, Calif., USA) and cryosections of 7 µm were cut with Cryostat Leica CM1950. Cryosections were washed with 1×PBS and fixated in 4% formaldehyde solution for 15 min (Catalog #: F555-4L, Sigma-Aldrich, Saint-Louis, Mo., USA) and then permeabilized with 0.02% SDS-PBS for 30 seconds. Blocking solution was 5%-Bovine Serum Albumin (BSA) in PBS. Primary antibodies were diluted in blocking solution and incubated overnight and indicated secondary antibodies were diluted in PBS for 30 minutes. Nuclei were counterstained with Hoechst (Catalog #: D1306, Invitrogen, Carlsbad, Calif., USA). Slides were then mounted with Vectashield® Mounting Medium (Catalog #: H-1000, Vector Laboratories, Burlingame, Calif., USA). Images were acquired and analyzed with Zeiss Imager.Z2 microscope equipped with either Zeiss AxioVision or Zeiss ZEN 2012 software (Carl Zeiss Inc., Oberkochen, Germany).

Anti-Collagen IV antibody, ab6586 from Abcam and LOXL2 antibody, GTX105085 from GeneTex were used.

For the electron microscopy imaging on the liver extracts, the samples were immersed in glutaraldehyde (2.5%) and paraformaldehyde (2.5%) in cacodylate buffer (0.1 M, pH 7.4). The samples were post-fixed in 1% osmium tetroxide, dehydrated through graded alcohol (50, 70, 90, and 100%) and propylene oxide for 30 minutes each, and embedded in Epon 812. Semithin sections were cut at 2 µm on an ultra microtome (Leica Ultracut UCT) and ultrathin sections were cut at 70 nm and contrasted with uranyl acetate and lead citrate and examined at 70 kv with a Morgagni 268D electron microscope. Images were captured digitally by Mega View III camera (Soft Imaging System).

Biochemical Assay

For the Plasma Determination

AST and ALT ELISA Measurements

Plasma samples from the indicated mice were used to determine plasma content of either AST (aspartate aminotransferase) or ASL (alanine aminotransferase) both robust indicators of liver damage were measured using commercially purchased ELISA kits. These parameters were determined according to manufacturer's procedure.

SEB214Mu (96 Tests): Enzyme-linked Immunosorbent Assay Kit For Aspartate Aminotransferase (AST), Cloud Clone Corp SEA207Mu (96 Tests): Enzyme-linked Immunosorbent Assay Kit For Alanine Aminotransferase (ALT), Cloud Clone Corp.

For LOXL2 and GLP-1 measurements, the two commercially available kits

Lysyl Oxydase Like Protein 2 (LOXL2), Enzyme-linked Immunosorbent Assay Kit, *Mus musculus*, SEF552Mu, Cloud Clone Corp RayBio Human/Mouse/Rat GLP-1 Enzyme Immunoassay Kit, EIA-GLP1, RayBiotech were used with the indicated procedures from the manufacturer.

For the measurements on the liver extracts, the same kit for LOXL2 was used and for FABP4, the commercial kit used was the Elisa kit for Fatty Acid Binding Protein 4, Adipocyte (FABP4), SEB693Mu, Cloud Clone Corp.

For the lipid composition in the different tissues and plasma, all samples were flashed frozen at the time of sampling, immediately after sacrifice, and were sent to the lipidomic core facility of Dijon, (Plateforme de Lipidomique-uBorgogne INSERM UMR866/Labex LipSTIC).

Example 13. In Vivo Efficacy Study of ADPIF Peptide in STAM Model of Non-Alcoholic Steatohepatitis Materials & Methods
Test Substances The peptide was ADPIF peptide as described above. The dosing solution was prepared according to the formulation instructions.

Induction of NASH

NASH was induced in 12 male mice by a single subcutaneous injection of 200 μg streptozotocin (STZ, Sigma-Aldrich, USA) solution 2 days after birth and feeding with high fat diet (HFD, 57 kcal % fat, Cat #HFD32, CLEA Japan, Inc., Japan) after 4 weeks of age.

Route of Drug Administration

The peptide was administered subcutaneously in the adipose tissue in a volume of 100 mL per mouse.

Treatment Dose

The peptide was administered at a dose of 25 microgram (m) per mouse once weekly.

Animals

C57BL/6 mice (14-day-pregnant female) were obtained from Japan SLC, Inc. (Japan). All animals used in the study were housed and cared for in accordance with the Japanese Pharmacological Society Guidelines for Animal Use.

The animals were maintained in a SPF facility under controlled conditions of temperature ($23\pm2°$ C.), humidity ($45\pm10\%$), lighting (12-hour artificial light and dark cycles; light from 8:00 to 20:00) and air exchange. A high pressure was maintained in the experimental room to prevent contamination of the facility.

The animals were housed in TPX cages (CLEA Japan) with a maximum of 3 mice per cage. Sterilized Paper-Clean (Japan SLC) was used for bedding and replaced once a week. Sterilized solid HFD was provided ad libitum, being placed in a metal lid on the top of the cage. Pure water was provided ad libitum from a water bottle equipped with a rubber stopper and a sipper tube. Water bottles were replaced once a week, cleaned, and sterilized in an autoclave and reused.

Mice were identified by ear punch. Each cage was labeled with a specific identification code.

Measurement of Plasma Biochemistry.

For plasma biochemistry, non-fasting blood was collected in polypropylene tubes with anticoagulant (Novo-Heparin, Mochida Pharmaceutical Co. Ltd., Japan) and centrifuged at $1,000\times g$ for 15 minutes at $4°$ C. The supernatant was collected and stored at $-80°$ C. until use. Plasma ALT level was measured by FUJI DRI-CHEM 7000 (Fujifilm, Japan).

Measurement of Liver Triglyceride Content

Liver total lipid-extracts were obtained by Folch's method (Folch J. et al., J. Biol. Chem. 1957; 226: 497). Liver samples were homogenized in chloroform-methanol (2:1, v/v) and incubated overnight at room temperature. After washing with chloroform-methanol-water (8:4:3, v/v/v), the extracts were evaporated to dryness, and dissolved in isopropanol. Liver triglyceride content was measured by Triglyceride E-test (Wako Pure Chemical Industries, Ltd., Japan).

Histological Analyses

For HE staining, sections were cut from paraffin blocks of liver tissue prefixed in Bouin's solution and stained with Lillie-Mayer's Hematoxylin (Muto Pure Chemicals Co., Ltd., Japan) and eosin solution (Wako Pure Chemical Industries). NAFLD Activity score (NAS) was calculated according to the criteria of Kleiner (Kleiner D E. et al., Hepatology, 2005; 41:1313).

To visualize collagen deposition, Bouin's fixed liver sections were stained using picro-Sirius red solution (Waldeck, Germany). For quantitative analysis of fibrosis area, bright field images of Sirius red-stained sections were captured around the central vein using a digital camera (DFC295; Leica, Germany) at 200-fold magnification, and the positive areas in 5 fields/section were measured using ImageJ software (National Institute of Health, USA).

Sample Collection

For plasma samples, the remaining plasma was collected and stored at $-80°$ C. for further analysis.

For liver samples, left lateral lobe was collected and cut into 6 pieces. Two pieces of left lateral lobe, left and right medial lobes, and caudate lobe were snap frozen in liquid nitrogen and stored at $-80°$ C. for further analysis. The other 2 pieces of left lateral lobe were fixed in Bouin's solution and then embedded in paraffin. Samples were stored at room temperature for histology. The remaining pieces of left lateral lobe were embedded in O.C.T. compound and quick frozen in liquid nitrogen. Samples were stored at $-80°$ C. for further analysis.

Statistical Tests

Statistical analyses were performed using Student's t-test on GraphPad Prism 6 (GraphPad Software Inc., USA). P values<0.05 were considered statistically significant. A trend or tendency was assumed when a one-tailed t-test returned P values<0.1. Results were expressed as mean±SD.

Experimental Design and Treatment
Study Groups
Group 1: ADPIF Peptide

Six NASH mice were subcutaneously in the adipose tissue administered vehicle supplemented with ADPIF peptide at a dose of 25 mg per mouse once weekly from 4 to 9 weeks of age.

Group 2: Vehicle

Six NASH mice were subcutaneously in the adipose tissue administered vehicle [DMSO in saline] in a volume of 100 mL per mouse once weekly from 4 to 9 weeks of age.

The table below summarizes the treatment schedule:

| Group | No. mice | Mice | Test substance | Dose (μg per mouse) | Volume (μl per mouse) | Regimen | Sacrifice (wks) |
|---|---|---|---|---|---|---|---|
| 1 | 6 | STAM | Test peptide | 25 | 100 | SC, QW, 4-9 wks | 9 |
| 2 | 6 | STAM | Vehicle | — | 100 | SC, QW, 4-9 wks | 9 |

Animal Monitoring and Sacrifice

The viability, clinical signs and behavior were monitored daily. Body weight was recorded before the treatment. Mice were observed for significant clinical signs of toxicity, moribundity and mortality approximately 60 minutes after each administration. The animals were sacrificed at 9 weeks of age by exsanguination through direct cardiac puncture under isoflurane anesthesia (Pfizer Inc.).

Results

Body Weight Changes and General Condition

Body weight changes

Mean body weight in all groups gradually increased during the treatment period. There were no significant differences in mean body weigh at any day during the treatment period between the ADPIF peptide group and the Vehicle group.

There were no dead animals in all groups during the treatment period. In the present study, none of the animals showed deterioration in general condition.

Liver triglyceride

The ADPIF peptide group showed a significant decrease in liver triglyceride content compared with the Vehicle group.

TABLE 1

| Biochemistry | | |
|---|---|---|
| Parameter (mean ± SD) | Test peptide (n = 6) | Vehicle (n = 6) |
| Plasma ALT (U/L) | 54 ± 9 | 55 ± 7 |
| Liver triglyceride (mg/g liver) | 35.1 ± 17.8 | 75.5 ± 33.0 |

Sirius red staining and the fibrosis area

Liver sections from the Vehicle group showed increased collagen deposition in the pericentral region of liver lobule. The ADPIF peptide group showed a significant decrease in the fibrosis area (Sirius red-positive area) compared with the Vehicle group.

TABLE 2

| Fibrosis area | | |
|---|---|---|
| Parameter (mean ± SD) | Test peptide (n = 6) | Vehicle (n = 6) |
| Sirius red-positive area (%) | 0.62 ± 0.17 | 0.92 ± 0.23 |

CONCLUSION

Treatment with ADPIF peptide showed significant decrease in liver triglyceride content and the fibrosis area compared with the Vehicle group. ADPIF peptide significantly reduced the fibrosis area compared with the Vehicle group, demonstrating an anti-fibrosis effect in the present study.

In conclusion, ADPIF peptide showed anti-fibrosis effects in this NASH model.

---

The invention claimed is:

1. A peptide wherein the peptide sequence comprises (SEQ ID NO: 32)
VECTTREKEVLASLDKAAFLTQLHS;

wherein R and S are stapled.

2. The peptide according to claim 1, wherein R is 2-(7-octenyl)arginine and S is 2-(4-pentenyl)serine.

3. A pharmaceutical composition comprising a peptide according to claim 1.

4. A method of treating a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis comprising the administration of a peptide according to claim 1, or a pharmaceutical composition thereof, to a subject in need of treatment.

5. The method according to claim 4, wherein the fibrosis is a liver fibrosis, liver cirrhosis, renal fibrosis, cardiac fibrosis, atrial fibrosis, endomyocardial fibrosis, old myocardial infarction, pulmonary fibrosis, cystic fibrosis, radio-induced lung fibrosis, vascular fibrosis, arterial fibrosis, brain fibrosis, myelofibrosis, arthrofibrosis, intestinal fibrosis, peritoneal fibrosis, retroperitoneal fibrosis or skin fibrosis.

6. A pharmaceutical composition comprising a peptide according to claim 2.

7. A method of treating a disease selected from the group consisting of nonalcoholic fatty liver disease (NAFLD), non-alcoholic fatty liver (NAFL), non-alcoholic steatohepatitis (NASH), hepatic steatosis (fatty liver), liver inflammation, cirrhosis, hepatocellular carcinoma and fibrosis comprising the administration of a peptide according to claim 2, or a pharmaceutical composition thereof, to a subject in need of treatment.

8. The method according to claim 7, wherein the fibrosis is a liver fibrosis, liver cirrhosis, renal fibrosis, cardiac fibrosis, atrial fibrosis, endomyocardial fibrosis, old myocardial infarction, pulmonary fibrosis, cystic fibrosis, radio-induced lung fibrosis, vascular fibrosis, arterial fibrosis, brain fibrosis, myelofibrosis, arthrofibrosis, intestinal fibrosis, peritoneal fibrosis, retroperitoneal fibrosis or skin fibrosis.

* * * * *

UNITED STATES PATENT AND TRADEMARK OFFICE
CERTIFICATE OF CORRECTION

PATENT NO. : 11,530,241 B2
APPLICATION NO. : 16/772178
DATED : December 20, 2022
INVENTOR(S) : Vincent Marion It is certified that error appears in the above-identified patent and that said Letters Patent is hereby corrected as shown below:

In the Specification

Column 5,
Line 50, "wherein R and S" should read --wherein R and S--.

Column 21,
Line 44, "underlined X" should read --underlined X--.
Line 59, "first X" should read --first X--.
Line 61, "second X" should read --second X--.

Column 22,
Line 6, "wherein R and S" should read --wherein R and S--.

Column 34,
Lines 49-50, "VECTTREKEVLASLDKAAFLTQLHS" should read
--VECTTREKEVLASLDKAAFLTQLHS--.
Line 51, "wherein R and S" should read --wherein R and S--.

In the Claims

Column 67,
Line 25, "wherein R and S" should read --wherein R and S--.

Signed and Sealed this
Fifteenth Day of August, 2023

Katherine Kelly Vidal
*Director of the United States Patent and Trademark Office*

SEQUENCE LISTING

<160> NUMBER OF SEQ ID NOS: 52

<210> SEQ ID NO 1
<211> LENGTH: 672
<212> TYPE: PRT
<213> ORGANISM: Homo sapiens

<400> SEQUENCE: 1

```
Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
                85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
        115                 120                 125

Gly Met Lys Cys Asp Thr Cys Asp Met Asn Val His Lys Gln Cys Val
    130                 135                 140

Ile Asn Val Pro Ser Leu Cys Gly Met Asp His Thr Glu Lys Arg Gly
```

-continued

```
           145                 150                 155                 160
        Arg Ile Tyr Leu Lys Ala Glu Val Ala Asp Glu Lys Leu His Val Thr
                            165                 170                 175

Val Arg Asp Ala Lys Asn Leu Ile Pro Met Asp Pro Asn Gly Leu Ser
                            180                 185                 190

Asp Pro Tyr Val Lys Leu Lys Leu Ile Pro Asp Pro Lys Asn Glu Ser
                            195                 200                 205

Lys Gln Lys Thr Lys Thr Ile Arg Ser Thr Leu Asn Pro Gln Trp Asn
                            210                 215                 220

Glu Ser Phe Thr Phe Lys Leu Lys Pro Ser Asp Lys Asp Arg Arg Leu
        225                 230                 235                 240

Ser Val Glu Ile Trp Asp Trp Asp Arg Thr Thr Arg Asn Asp Phe Met
                            245                 250                 255

Gly Ser Leu Ser Phe Gly Val Ser Glu Leu Met Lys Met Pro Ala Ser
                            260                 265                 270

Gly Trp Tyr Lys Leu Leu Asn Gln Glu Glu Gly Glu Tyr Tyr Asn Val
                            275                 280                 285

Pro Ile Pro Glu Gly Asp Glu Gly Asn Met Glu Leu Arg Gln Lys
                            290                 295                 300

Phe Glu Lys Ala Lys Leu Gly Pro Ala Gly Asn Lys Val Ile Ser Pro
        305                 310                 315                 320

Ser Glu Asp Arg Lys Gln Pro Ser Asn Asn Leu Asp Arg Val Lys Leu
                            325                 330                 335

Thr Asp Phe Asn Phe Leu Met Val Leu Gly Lys Gly Ser Phe Gly Lys
                            340                 345                 350

Val Met Leu Ala Asp Arg Lys Gly Thr Glu Glu Leu Tyr Ala Ile Lys
                            355                 360                 365

Ile Leu Lys Lys Asp Val Val Ile Gln Asp Asp Val Glu Cys Thr
                            370                 375                 380

Met Val Glu Lys Arg Val Leu Ala Leu Leu Asp Lys Pro Pro Phe Leu
        385                 390                 395                 400

Thr Gln Leu His Ser Cys Phe Gln Thr Val Asp Arg Leu Tyr Phe Val
                            405                 410                 415

Met Glu Tyr Val Asn Gly Gly Asp Leu Met Tyr His Ile Gln Gln Val
                            420                 425                 430

Gly Lys Phe Lys Glu Pro Gln Ala Val Phe Tyr Ala Ala Glu Ile Ser
                            435                 440                 445

Ile Gly Leu Phe Phe Leu His Lys Arg Gly Ile Ile Tyr Arg Asp Leu
        450                 455                 460

Lys Leu Asp Asn Val Met Leu Asp Ser Glu Gly His Ile Lys Ile Ala
        465                 470                 475                 480

Asp Phe Gly Met Cys Lys Glu His Met Met Asp Gly Val Thr Thr Arg
                            485                 490                 495

Thr Phe Cys Gly Thr Pro Asp Tyr Ile Ala Pro Glu Ile Ile Ala Tyr
                            500                 505                 510

Gln Pro Tyr Gly Lys Ser Val Asp Trp Trp Ala Tyr Gly Val Leu Leu
                            515                 520                 525

Tyr Glu Met Leu Ala Gly Gln Pro Pro Phe Asp Gly Glu Asp Glu Asp
                            530                 535                 540

Glu Leu Phe Gln Ser Ile Met Glu His Asn Val Ser Tyr Pro Lys Ser
        545                 550                 555                 560

Leu Ser Lys Glu Ala Val Ser Val Cys Lys Gly Leu Met Thr Lys His
                            565                 570                 575
```

```
Pro Ala Lys Arg Leu Gly Cys Gly Pro Glu Gly Arg Asp Val Arg
            580                 585                 590

Glu His Ala Phe Phe Arg Arg Ile Asp Trp Glu Lys Leu Glu Asn Arg
            595                 600                 605

Glu Ile Gln Pro Pro Phe Lys Pro Lys Val Cys Gly Lys Gly Ala Glu
610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
                660                 665                 670
```

<210> SEQ ID NO 2
<211> LENGTH: 257
<212> TYPE: PRT
<213> ORGANISM: Homo sapiens

<400> SEQUENCE: 2

```
Phe Asn Phe Leu Met Val Leu Gly Lys Gly Ser Phe Gly Lys Val Met
1               5                   10                  15

Leu Ala Asp Arg Lys Gly Thr Glu Glu Leu Tyr Ala Ile Lys Ile Leu
                20                  25                  30

Lys Lys Asp Val Val Ile Gln Asp Asp Val Glu Cys Thr Met Val
            35                  40                  45

Glu Lys Arg Val Leu Ala Leu Leu Asp Lys Pro Pro Phe Leu Thr Gln
50                  55                  60

Leu His Ser Cys Phe Gln Thr Val Asp Arg Leu Tyr Phe Val Met Glu
65                  70                  75                  80

Tyr Val Asn Gly Gly Asp Leu Met Tyr His Ile Gln Gln Val Gly Lys
                85                  90                  95

Phe Lys Glu Pro Gln Ala Val Phe Tyr Ala Ala Glu Ile Ser Ile Gly
            100                 105                 110

Leu Phe Phe Leu His Lys Arg Gly Ile Ile Tyr Arg Asp Leu Lys Leu
        115                 120                 125

Asp Asn Val Met Leu Asp Ser Glu Gly His Ile Lys Ile Ala Asp Phe
130                 135                 140

Gly Met Cys Lys Glu His Met Met Asp Gly Val Thr Thr Arg Thr Phe
145                 150                 155                 160

Cys Gly Thr Pro Asp Tyr Ile Ala Pro Glu Ile Ile Ala Tyr Gln Pro
                165                 170                 175

Tyr Gly Lys Ser Val Asp Trp Trp Ala Tyr Gly Val Leu Leu Tyr Glu
            180                 185                 190

Met Leu Ala Gly Gln Pro Pro Phe Asp Gly Glu Asp Glu Asp Glu Leu
        195                 200                 205

Phe Gln Ser Ile Met Glu His Asn Val Ser Tyr Pro Lys Ser Leu Ser
210                 215                 220

Lys Glu Ala Val Ser Val Cys Lys Gly Leu Met Thr Lys His Pro Ala
225                 230                 235                 240

Lys Arg Leu Gly Cys Gly Pro Glu Gly Glu Arg Asp Val Arg Glu His
                245                 250                 255

Ala
```

<210> SEQ ID NO 3

```
<211> LENGTH: 12
<212> TYPE: PRT
<213> ORGANISM: artificial sequence
<220> FEATURE:
<223> OTHER INFORMATION: segment of kinase domain of alphaPKC

<400> SEQUENCE: 3

Val Glu Cys Thr Met Val Glu Lys Arg Val Leu Ala
1               5                   10

<210> SEQ ID NO 4
<211> LENGTH: 8
<212> TYPE: PRT
<213> ORGANISM: artificial sequence
<220> FEATURE:
<223> OTHER INFORMATION: segment of kinase domain of alphaPKC

<400> SEQUENCE: 4

Leu Met Tyr His Ile Gln Gln Val
1               5

<210> SEQ ID NO 5
<211> LENGTH: 4
<212> TYPE: PRT
<213> ORGANISM: artificial sequence
<220> FEATURE:
<223> OTHER INFORMATION: segment of kinase domain of alphaPKC

<400> SEQUENCE: 5

Pro Glu Ile Ile
1

<210> SEQ ID NO 6
<211> LENGTH: 16
<212> TYPE: PRT
<213> ORGANISM: artificial sequence
<220> FEATURE:
<223> OTHER INFORMATION: segment of kinase domain of alphaPKC

<400> SEQUENCE: 6

Ser Val Asp Trp Trp Ala Tyr Gly Val Leu Leu Tyr Glu Met Leu Ala
1               5                   10                  15

<210> SEQ ID NO 7
<211> LENGTH: 12
<212> TYPE: PRT
<213> ORGANISM: artificial sequence
<220> FEATURE:
<223> OTHER INFORMATION: segment of kinase domain of alphaPKC

<400> SEQUENCE: 7

Glu Asp Glu Asp Glu Leu Phe Gln Ser Ile Met Glu
1               5                   10

<210> SEQ ID NO 8
<211> LENGTH: 7
<212> TYPE: PRT
<213> ORGANISM: artificial sequence
<220> FEATURE:
<223> OTHER INFORMATION: segment of kinase domain of alphaPKC

<400> SEQUENCE: 8

Gly Glu Arg Asp Val Arg Glu
1               5

<210> SEQ ID NO 9
<211> LENGTH: 12
```

```
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except R, M and P

<400> SEQUENCE: 9

Val Glu Cys Thr Xaa Val Glu Lys Arg Val Leu Ala
1               5                   10

<210> SEQ ID NO 10
<211> LENGTH: 12
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (9)..(9)
<223> OTHER INFORMATION: Xaa is any amino acid except M, P and R

<400> SEQUENCE: 10

Val Glu Cys Thr Met Val Glu Lys Xaa Val Leu Ala
1               5                   10

<210> SEQ ID NO 11
<211> LENGTH: 12
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (9)..(9)
<223> OTHER INFORMATION: Xaa is any amino acid except M, P and R

<400> SEQUENCE: 11

Val Glu Cys Thr Xaa Val Glu Lys Xaa Val Leu Ala
1               5                   10

<210> SEQ ID NO 12
<211> LENGTH: 8
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (2)..(2)
<223> OTHER INFORMATION: Xaa is any amino acid except M, P and R

<400> SEQUENCE: 12

Leu Xaa Tyr His Ile Gln Gln Val
1               5

<210> SEQ ID NO 13
<211> LENGTH: 16
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (14)..(14)
```

<223> OTHER INFORMATION: Xaa is any amino acid except M, P and R

<400> SEQUENCE: 13

Ser Val Asp Trp Trp Ala Tyr Gly Val Leu Leu Tyr Glu Xaa Leu Ala
1               5                   10                  15

<210> SEQ ID NO 14
<211> LENGTH: 12
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (11)..(11)
<223> OTHER INFORMATION: Xaa is any amino acid except M, P and R

<400> SEQUENCE: 14

Glu Asp Glu Asp Glu Leu Phe Gln Ser Ile Xaa Glu
1               5                   10

<210> SEQ ID NO 15
<211> LENGTH: 7
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (3)..(3)
<223> OTHER INFORMATION: Xaa is any amino acid except M, P and R

<400> SEQUENCE: 15

Gly Glu Xaa Asp Val Arg Glu
1               5

<210> SEQ ID NO 16
<211> LENGTH: 7
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid except M, P and R

<400> SEQUENCE: 16

Gly Glu Arg Asp Val Xaa Glu
1               5

<210> SEQ ID NO 17
<211> LENGTH: 7
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (3)..(3)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid except M, P and R

<400> SEQUENCE: 17

Gly Glu Xaa Asp Val Xaa Glu
1               5

```
<210> SEQ ID NO 18
<211> LENGTH: 4
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (1)..(1)
<223> OTHER INFORMATION: Xaa is any amino acid except M, P and R

<400> SEQUENCE: 18

Xaa Glu Ile Ile
1

<210> SEQ ID NO 19
<211> LENGTH: 12
<212> TYPE: PRT
<213> ORGANISM: artificial sequence
<220> FEATURE:
<223> OTHER INFORMATION: mutated segment of kinase domain of alphaPKC

<400> SEQUENCE: 19

Val Glu Cys Thr Thr Val Glu Lys Glu Val Leu Ala
1               5                   10

<210> SEQ ID NO 20
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 20

Val Glu Cys Thr Xaa Val Glu Lys Xaa Val Leu Ala Leu Leu Asp Lys
1               5                   10                  15

Xaa Xaa Phe Leu Thr Gln Leu His Ser
            20                  25

<210> SEQ ID NO 21
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 21

Val Glu Cys Thr Met Val Glu Lys Arg Val Leu Ala Leu Leu Asp Lys
1               5                   10                  15

Xaa Xaa Phe Leu Thr Gln Leu His Ser
            20                  25
```

```
<210> SEQ ID NO 22
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R

<400> SEQUENCE: 22

Val Glu Cys Thr Xaa Val Glu Lys Arg Val Leu Ala Leu Leu Asp Lys
1               5                   10                  15

Pro Pro Phe Leu Thr Gln Leu His Ser
            20                  25

<210> SEQ ID NO 23
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (9)..(9)
<223> OTHER INFORMATION: Xaa is any amino acid except M, P and R

<400> SEQUENCE: 23

Val Glu Cys Thr Met Val Glu Lys Xaa Val Leu Ala Leu Leu Asp Lys
1               5                   10                  15

Pro Pro Phe Leu Thr Gln Leu His Ser
            20                  25

<210> SEQ ID NO 24
<211> LENGTH: 13
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 24

Val Glu Cys Thr Met Xaa Glu Lys Arg Val Leu Ala Xaa
1               5                   10

<210> SEQ ID NO 25
<211> LENGTH: 13
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
```

```
<221> NAME/KEY: MISC_FEATURE
<222> LOCATION: (13)..(13)
<223> OTHER INFORMATION: Xaa is any amino acid derivative suitable for
      stapling

<400> SEQUENCE: 25

Val Glu Cys Thr Xaa Xaa Glu Lys Arg Val Leu Ala Xaa
1               5                   10

<210> SEQ ID NO 26
<211> LENGTH: 13
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 26

Val Glu Cys Thr Met Xaa Glu Lys Xaa Val Leu Ala Xaa
1               5                   10

<210> SEQ ID NO 27
<211> LENGTH: 13
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 27

Val Glu Cys Thr Xaa Xaa Glu Lys Xaa Val Leu Ala Xaa
1               5                   10

<210> SEQ ID NO 28
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
```

```
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 28

Val Glu Cys Thr Xaa Xaa Glu Lys Xaa Val Leu Ala Xaa Leu Asp Lys
1               5                   10                  15

Xaa Xaa Phe Leu Thr Gln Leu His Ser
            20                  25

<210> SEQ ID NO 29
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling
<220> FEATURE:
<221> NAME/KEY: MISC_FEATURE
<222> LOCATION: (17)..(18)
<223> OTHER INFORMATION: Xaa is any amino acid except M, P and R

<400> SEQUENCE: 29

Val Glu Cys Thr Met Xaa Glu Lys Arg Val Leu Ala Xaa Leu Asp Lys
1               5                   10                  15

Xaa Xaa Phe Leu Thr Gln Leu His Ser
            20                  25

<210> SEQ ID NO 30
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (5)..(5)
<223> OTHER INFORMATION: Xaa is any amino acid except M, P and R
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling
```

```
<400> SEQUENCE: 30

Val Glu Cys Thr Xaa Xaa Glu Lys Arg Val Leu Ala Xaa Leu Asp Lys
1               5                   10                  15

Pro Pro Phe Leu Thr Gln Leu His Ser
            20                  25

<210> SEQ ID NO 31
<211> LENGTH: 25
<212> TYPE: PRT
<213> ORGANISM: artificial sequence
<220> FEATURE:
<223> OTHER INFORMATION: mutated segment of kinase domain of alphaPKC
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid except M, P and R
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 31

Val Glu Cys Thr Met Xaa Glu Lys Xaa Val Leu Ala Xaa Leu Asp Lys
1               5                   10                  15

Pro Pro Phe Leu Thr Gln Leu His Ser
            20                  25

<210> SEQ ID NO 32
<211> LENGTH: 25
<212> TYPE: PRT
<213> ORGANISM: artificial sequence
<220> FEATURE:
<223> OTHER INFORMATION: mutated segment of kinase domain of alphaPKC

<400> SEQUENCE: 32

Val Glu Cys Thr Thr Arg Glu Lys Glu Val Leu Ala Ser Leu Asp Lys
1               5                   10                  15

Ala Ala Phe Leu Thr Gln Leu His Ser
            20                  25

<210> SEQ ID NO 33
<211> LENGTH: 8
<212> TYPE: PRT
<213> ORGANISM: artificial sequence
<220> FEATURE:
<223> OTHER INFORMATION: protein transduction domain

<400> SEQUENCE: 33

Arg Arg Arg Arg Arg Arg Arg Arg
1               5

<210> SEQ ID NO 34
<211> LENGTH: 15
<212> TYPE: PRT
<213> ORGANISM: artificial sequence
<220> FEATURE:
<223> OTHER INFORMATION: protein transduction domain

<400> SEQUENCE: 34

Arg Arg Pro Arg Arg Pro Arg Arg Pro Arg Arg Pro Arg Arg Pro
1               5                   10                  15
```

```
<210> SEQ ID NO 35
<211> LENGTH: 16
<212> TYPE: PRT
<213> ORGANISM: artificial sequence
<220> FEATURE:
<223> OTHER INFORMATION: penetratin peptide

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 11
<212> TYPE: PRT
<213> ORGANISM: artificial sequence
<220> FEATURE:
<223> OTHER INFORMATION: HIV-tat

<400> SEQUENCE: 36

Tyr Gly Arg Lys Lys Arg Arg Gln Arg Arg Arg
1               5                   10

<210> SEQ ID NO 37
<211> LENGTH: 20
<212> TYPE: DNA
<213> ORGANISM: artificial sequence
<220> FEATURE:
<223> OTHER INFORMATION: primer

<400> SEQUENCE: 37
tgctttggtt tctgggactt                                              20

<210> SEQ ID NO 38
<211> LENGTH: 20
<212> TYPE: DNA
<213> ORGANISM: artificial sequence
<220> FEATURE:
<223> OTHER INFORMATION: primer

<400> SEQUENCE: 38
gctctagccg aacacgaatc                                              20

<210> SEQ ID NO 39
<211> LENGTH: 22
<212> TYPE: DNA
<213> ORGANISM: artificial sequence
<220> FEATURE:
<223> OTHER INFORMATION: primer

<400> SEQUENCE: 39
tggacaaagt agacggagtg tc                                           22

<210> SEQ ID NO 40
<211> LENGTH: 20
<212> TYPE: DNA
<213> ORGANISM: artificial sequence
<220> FEATURE:
<223> OTHER INFORMATION: primer

<400> SEQUENCE: 40
tagcaaggcc tgtcccatac                                              20

<210> SEQ ID NO 41
<211> LENGTH: 20
<212> TYPE: DNA
```

```
<213> ORGANISM: artificial sequence
<220> FEATURE:
<223> OTHER INFORMATION: primer

<400> SEQUENCE: 41
tgagaacttg ccaccgtatg                                               20

<210> SEQ ID NO 42
<211> LENGTH: 20
<212> TYPE: DNA
<213> ORGANISM: artificial sequence
<220> FEATURE:
<223> OTHER INFORMATION: primer

<400> SEQUENCE: 42
ggcaggtagg ccctatatc                                                20

<210> SEQ ID NO 43
<211> LENGTH: 20
<212> TYPE: DNA
<213> ORGANISM: artificial sequence
<220> FEATURE:
<223> OTHER INFORMATION: primer

<400> SEQUENCE: 43
gtttcatccg ggtcttcatc                                               20

<210> SEQ ID NO 44
<211> LENGTH: 20
<212> TYPE: DNA
<213> ORGANISM: artificial sequence
<220> FEATURE:
<223> OTHER INFORMATION: primer

<400> SEQUENCE: 44
gtgtctgtgc cctcgaaaat                                               20

<210> SEQ ID NO 45
<211> LENGTH: 20
<212> TYPE: DNA
<213> ORGANISM: artificial sequence
<220> FEATURE:
<223> OTHER INFORMATION: primer

<400> SEQUENCE: 45
aagttctctg cctcccgatt                                               20

<210> SEQ ID NO 46
<211> LENGTH: 20
<212> TYPE: DNA
<213> ORGANISM: artificial sequence
<220> FEATURE:
<223> OTHER INFORMATION: primer

<400> SEQUENCE: 46
caaagcgttg ctggaagttt                                               20

<210> SEQ ID NO 47
<211> LENGTH: 20
<212> TYPE: DNA
<213> ORGANISM: artificial sequence
<220> FEATURE:
<223> OTHER INFORMATION: primer

<400> SEQUENCE: 47
tcgattccct cctacactgc                                               20
```

<210> SEQ ID NO 48
<211> LENGTH: 20
<212> TYPE: DNA
<213> ORGANISM: artificial sequence
<220> FEATURE:
<223> OTHER INFORMATION: primer

<400> SEQUENCE: 48
ttggtggtac tggctcatca                                        20

<210> SEQ ID NO 49
<211> LENGTH: 25
<212> TYPE: PRT
<213> ORGANISM: ARTIFICIAL
<220> FEATURE:
<223> OTHER INFORMATION: Stapled peptide sequence A
<220> FEATURE:
<221> NAME/KEY: MISC_FEATURE
<222> LOCATION: (6)..(6)
<223> OTHER INFORMATION: Xaa is any amino acid derivative suitable for
      stapling
<220> FEATURE:
<221> NAME/KEY: MISC_FEATURE
<222> LOCATION: (13)..(13)
<223> OTHER INFORMATION: Xaa is any amino acid derivative suitable for
      stapling

<400> SEQUENCE: 49

Val Glu Cys Thr Met Xaa Glu Lys Arg Val Leu Ala Xaa Leu Asp Lys
1               5                   10                  15

Pro Pro Phe Leu Thr Gln Leu His Ser
            20                  25

<210> SEQ ID NO 50
<211> LENGTH: 21
<212> TYPE: PRT
<213> ORGANISM: artificial
<220> FEATURE:
<223> OTHER INFORMATION: Stapled peptide sequence B
<220> FEATURE:
<221> NAME/KEY: MISC_FEATURE
<222> LOCATION: (2)..(2)
<223> OTHER INFORMATION: Xaa is any amino acid derivative suitable for
      stapling
<220> FEATURE:
<221> NAME/KEY: MISC_FEATURE
<222> LOCATION: (9)..(9)
<223> OTHER INFORMATION: Xaa is any amino acid derivative suitable for
      stapling

<400> SEQUENCE: 50

Ser Xaa Cys Lys Gly Leu Met Thr Xaa His Pro Ala Lys Arg Leu Gly
1               5                   10                  15

Cys Gly Pro Glu Gly
            20

<210> SEQ ID NO 51
<211> LENGTH: 26
<212> TYPE: PRT
<213> ORGANISM: artificial
<220> FEATURE:
<223> OTHER INFORMATION: Scrambled peptide sequence A

<400> SEQUENCE: 51

Lys Glu Val Pro Val Asp Thr Cys His Leu Thr Leu Met Leu Leu Phe
1               5                   10                  15

Arg Ser Val Ala Leu Lys Gln His Pro Glu

```
<210> SEQ ID NO 52
<211> LENGTH: 21
<212> TYPE: PRT
<213> ORGANISM: artificial
<220> FEATURE:
<223> OTHER INFORMATION: Scrambled peptide sequence B

<400> SEQUENCE: 52

Ser Ala Glu Cys Lys Gly Arg His Gly Thr Pro Pro Gly Lys Leu Met
1               5                   10                  15

Ile Cys Lys Gly Leu
            20
```